United States Patent
Murali et al.

(10) Patent No.: US 10,245,298 B2
(45) Date of Patent: Apr. 2, 2019

(54) COMPOSITIONS AND METHODS FOR TREATING FIBROSIS

(71) Applicants: Cedars-Sinai Medical Center, Los Angeles, CA (US); The Board of Trustees of the Leland Stanford Junior University, Palo Alto, CA (US)

(72) Inventors: Ramachandran Murali, Swarthmore, PA (US); Aida Habtezion, Sunnyvale, CA (US); Stephen J. Pandol, Los Angeles, CA (US)

(73) Assignees: Cedars-Sinai Medical Center, Los Angeles, CA (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/460,151

(22) Filed: Mar. 15, 2017

(65) Prior Publication Data

US 2017/0189471 A1    Jul. 6, 2017

Related U.S. Application Data

(63) Continuation-in-part of application No. PCT/US2015/050906, filed on Sep. 18, 2015.

(60) Provisional application No. 62/052,111, filed on Sep. 18, 2014.

(51) Int. Cl.
| | |
|---|---|
| *A61K 38/00* | (2006.01) |
| *A61P 35/00* | (2006.01) |
| *A61K 38/10* | (2006.01) |
| *C07K 14/54* | (2006.01) |
| *A61N 5/10* | (2006.01) |

(52) U.S. Cl.
CPC ............ *A61K 38/10* (2013.01); *A61N 5/1001* (2013.01); *C07K 14/5406* (2013.01); *C07K 14/5437* (2013.01)

(58) Field of Classification Search
CPC ... A61K 38/10; A61K 38/202; A61K 38/2026
See application file for complete search history.

(56) References Cited

U.S. PATENT DOCUMENTS

| 7,410,781 B2 | 8/2008 | Karow et al. |
| 2003/0124121 A1 | 7/2003 | Pluenneke |
| 2011/0183920 A1 | 7/2011 | Pan et al. |
| 2011/0256130 A1 | 10/2011 | Schultz et al. |
| 2011/0268749 A1 | 11/2011 | Strober et al. |
| 2012/0156194 A1 | 6/2012 | Aaron et al. |
| 2013/0209541 A1 | 8/2013 | Debinski et al. |
| 2013/0259866 A1 | 10/2013 | Rao et al. |

FOREIGN PATENT DOCUMENTS

| WO | 2000064944 A1 | 11/2000 |
| WO | 2000078336 A1 | 12/2000 |
| WO | 01/34645 A2 | 5/2001 |
| WO | 2009043518 A2 | 4/2009 |
| WO | 2012162592 A1 | 11/2012 |
| WO | 2016044707 A1 | 3/2016 |

OTHER PUBLICATIONS

PCT/US2015/050906 International Search Report and Written Opinion dated Dec. 18, 2015; 12 pages.
Mueller et al. Structure, binding, and antagonists in the IL-4/IL-13 receptor system. Biochimica et Biophysica Acta (2002). 1592:237-250.
Oh et al. Investigational therapeutics targeting the IL-4/IL-13/STAT-6 pathway for the treatment of asthma. Eur Respir Rev (2010). 19(115):46-54.
PCT/US2015/050906 International Preliminary Report on Patentability dated Mar. 21, 2017; 10 pages.

*Primary Examiner* — Rachael E Bredefeld
*Assistant Examiner* — Kaipeen E Yang
(74) *Attorney, Agent, or Firm* — JHK Law; Joseph Hyosuk Kim

(57) ABSTRACT

The invention provides methods for treating fibrosis and/or cancer in a subject in need thereof. The methods include providing a composition comprising an inhibitor of IL-4/IL-13 receptor function and administering an effective amount of the composition to the subject to treat fibrosis and/or cancer.

6 Claims, 21 Drawing Sheets

Specification includes a Sequence Listing.

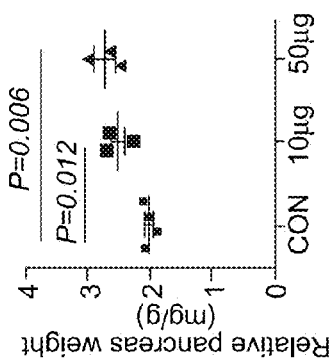
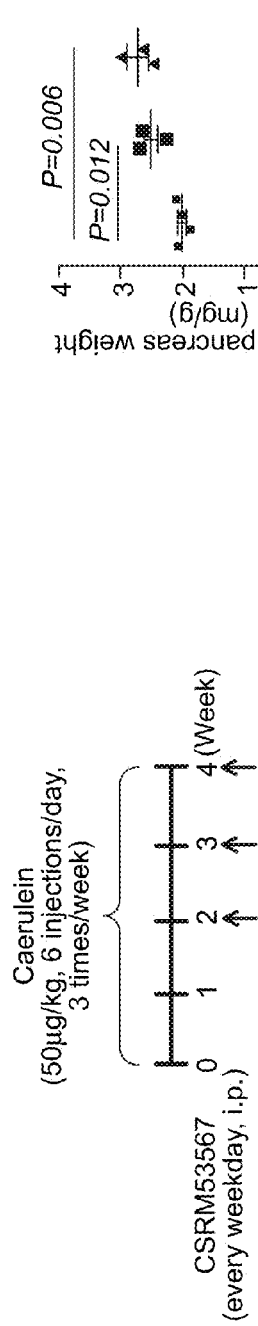
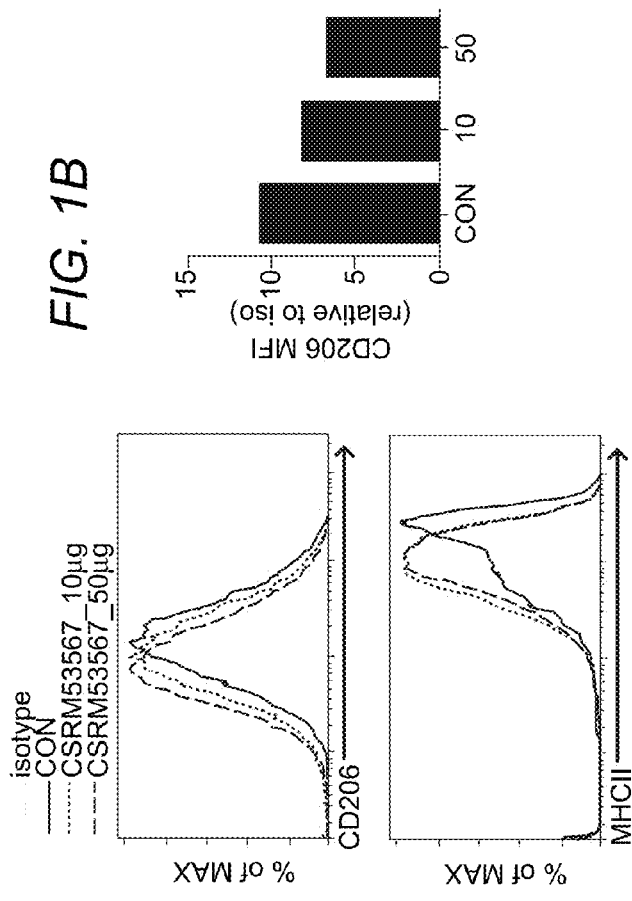

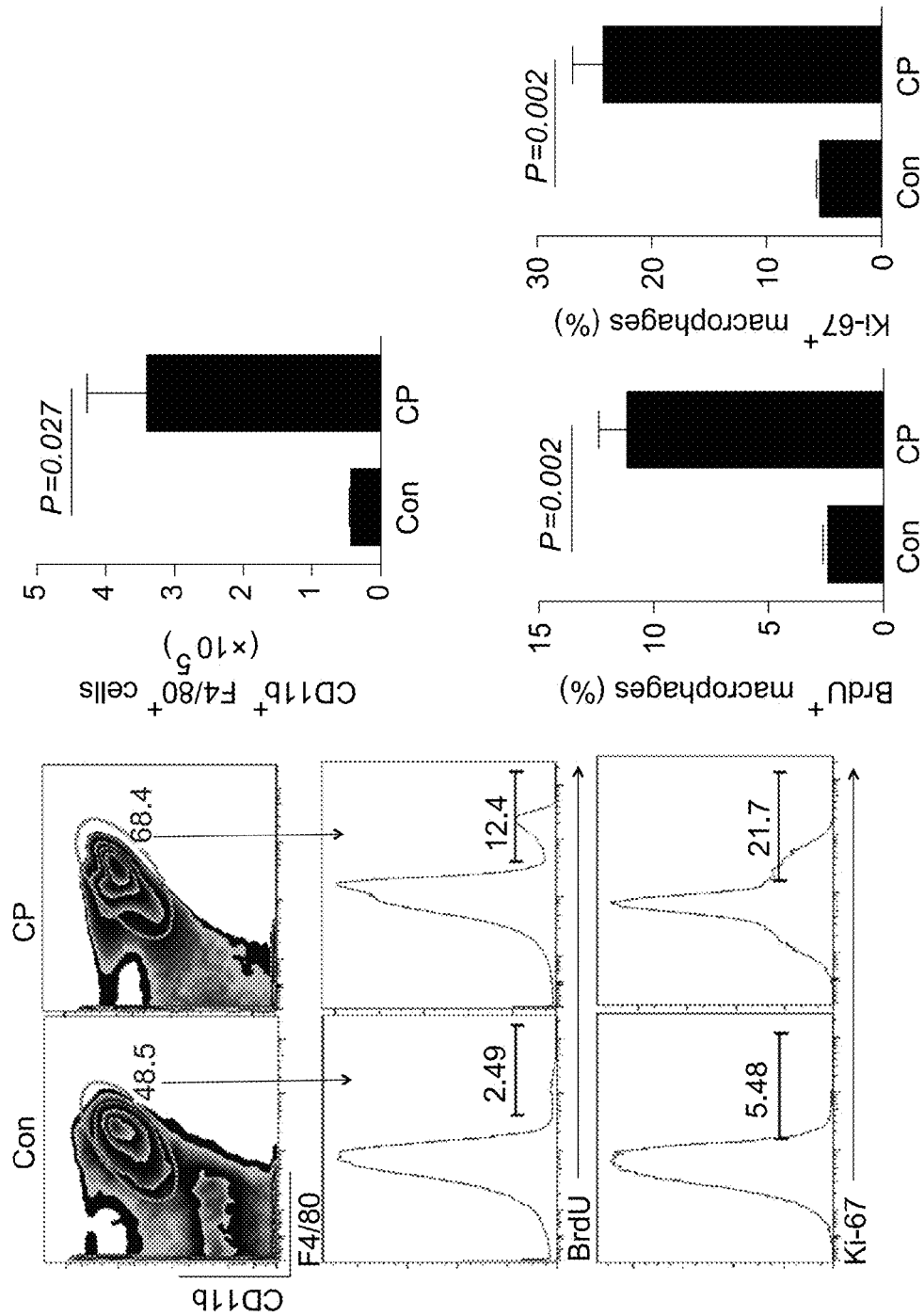

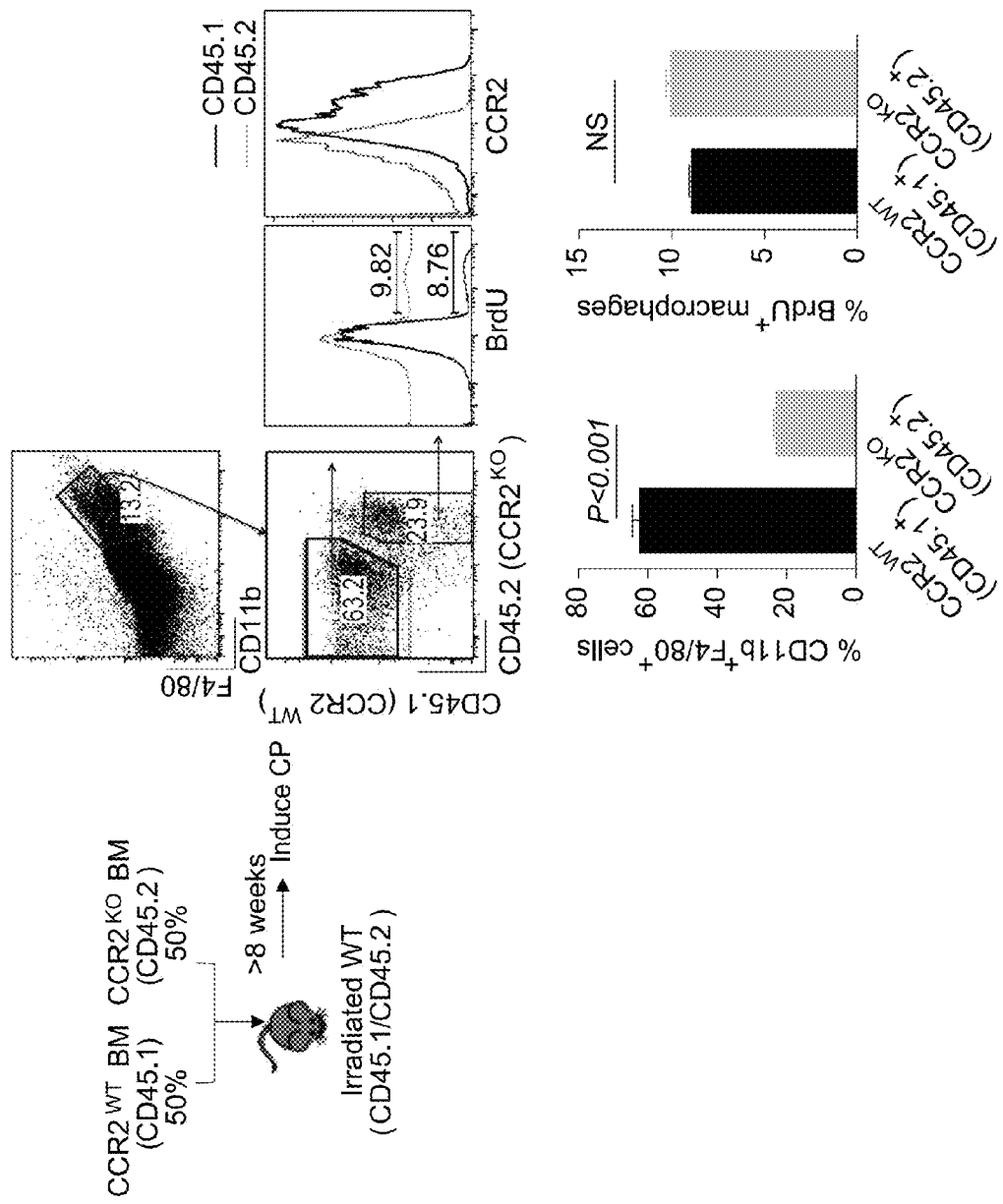

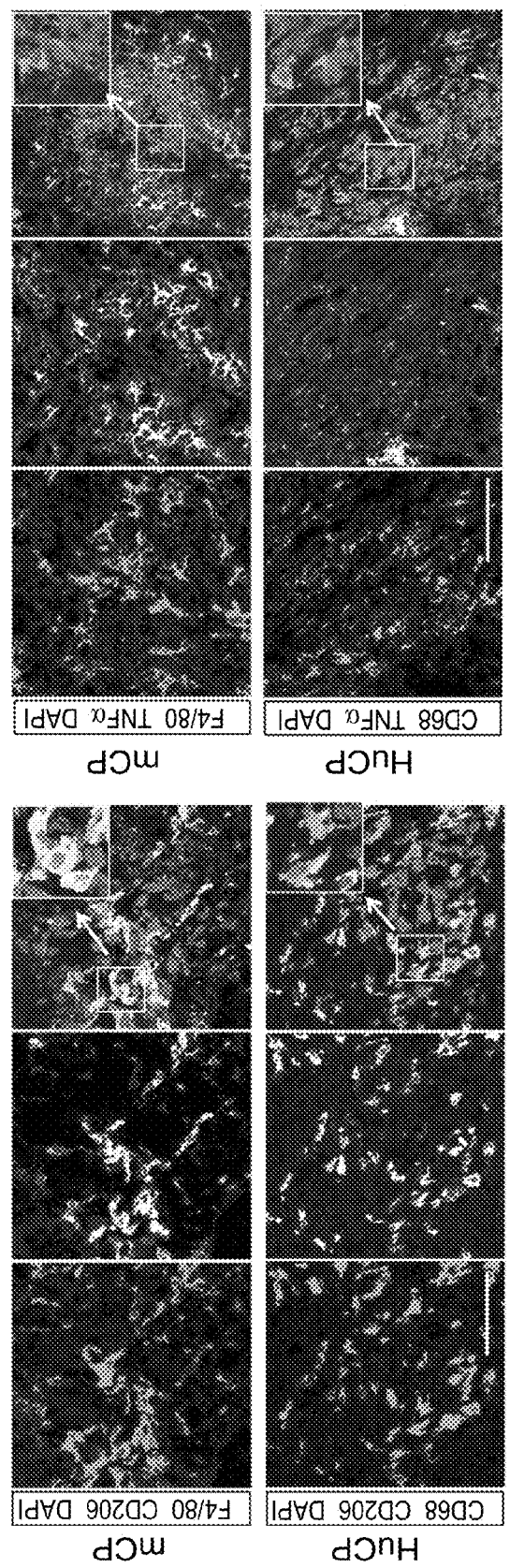

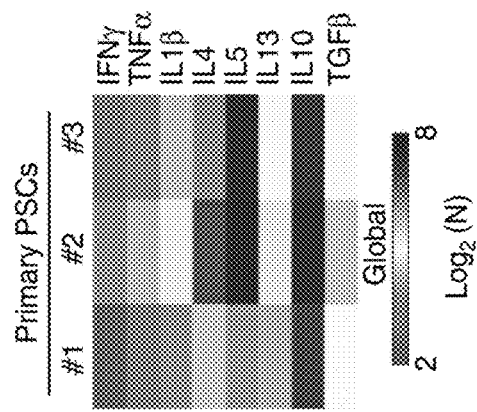
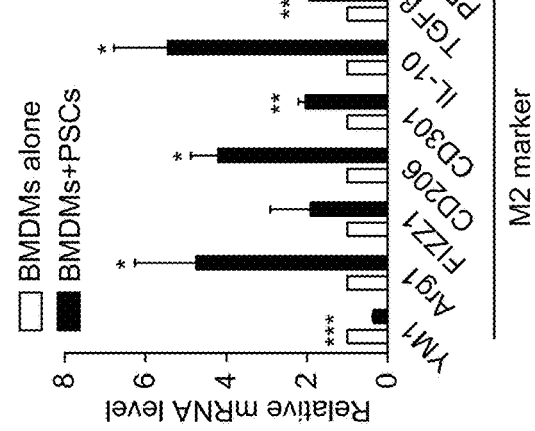
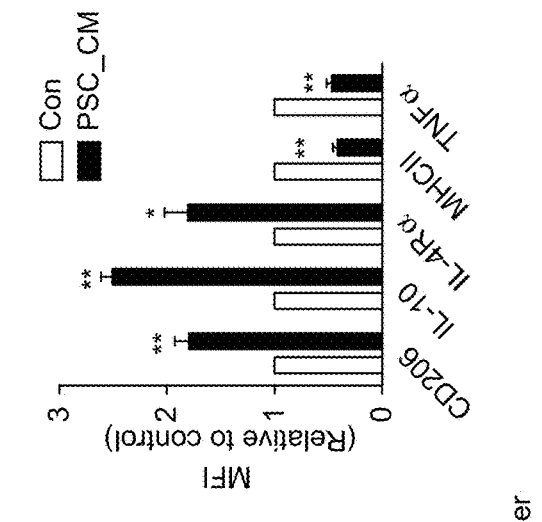
FIG. 4A
FIG. 4B
FIG. 4C

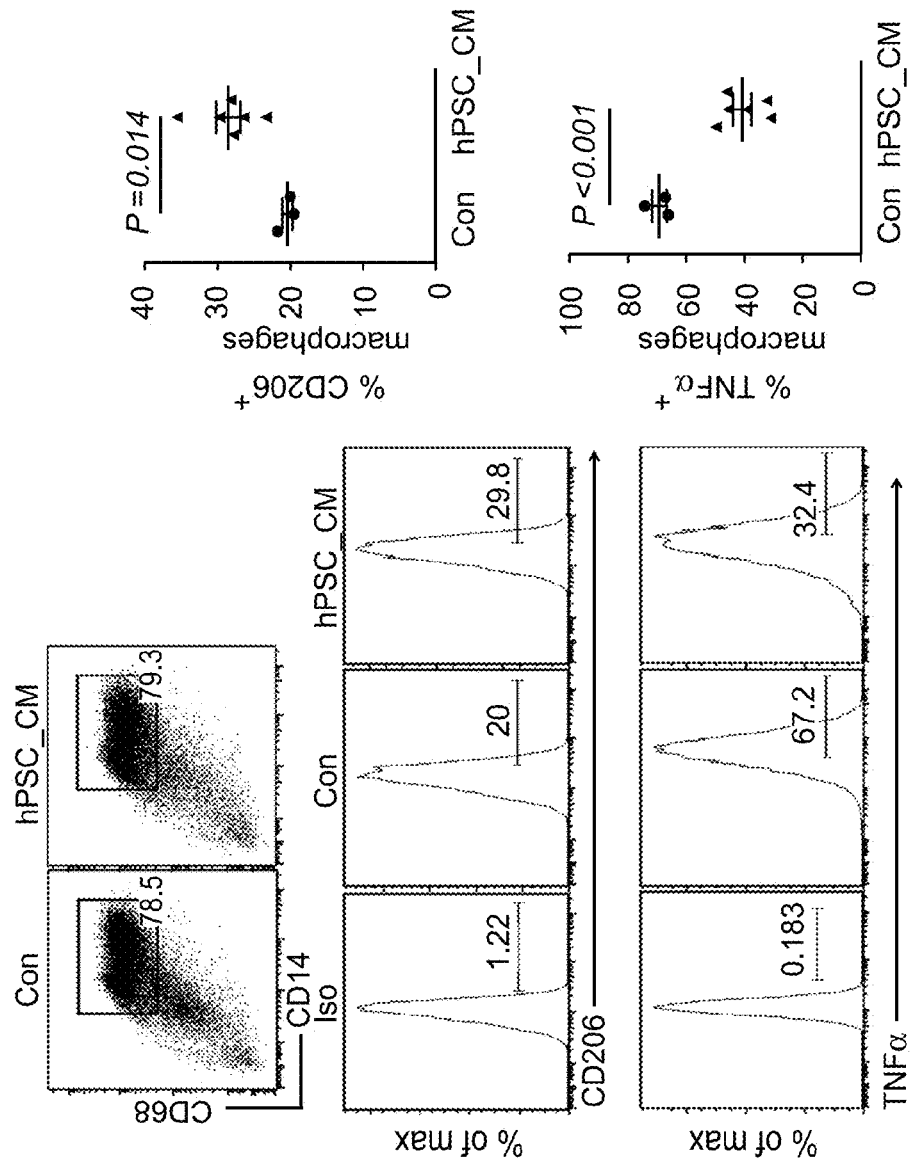
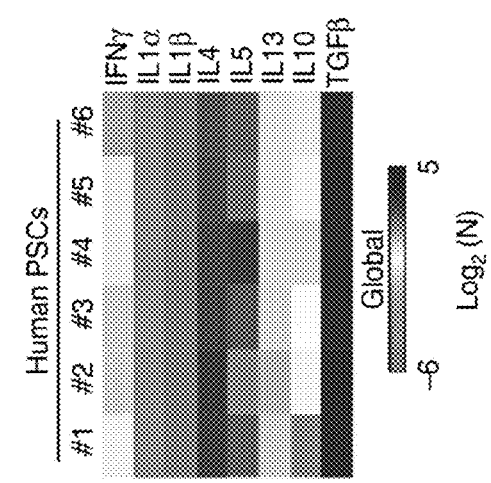
FIG. 4G
FIG. 4F

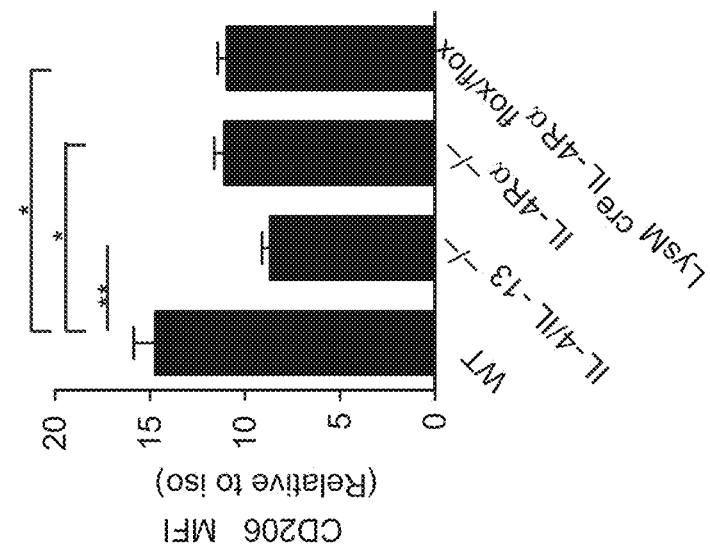
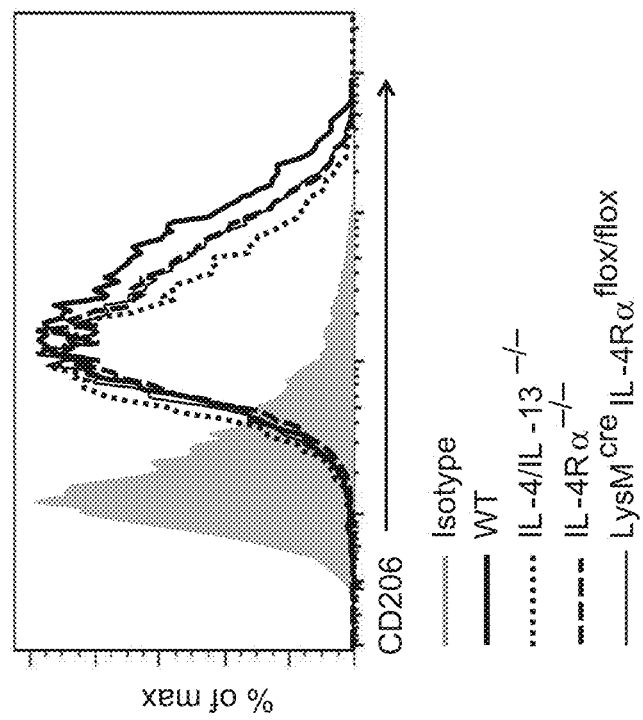
FIG. 5F

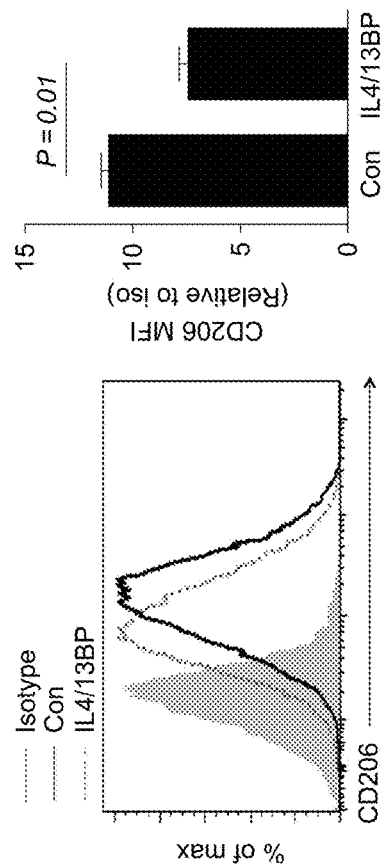
FIG. 6F
FIG. 6E
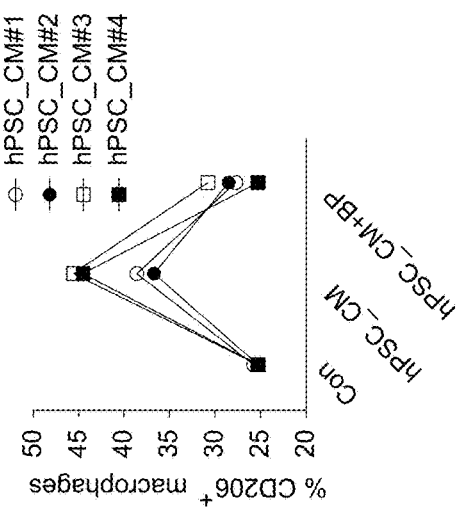
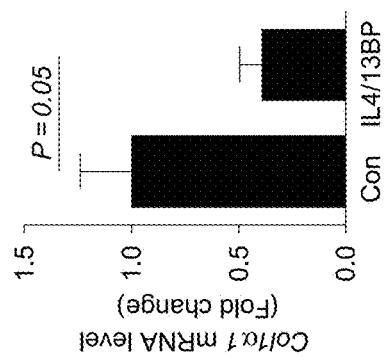
FIG. 6G
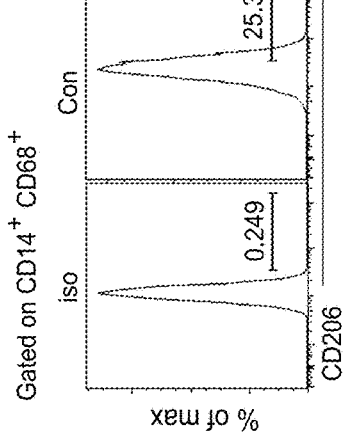

COMPOSITIONS AND METHODS FOR TREATING FIBROSIS

CROSS-REFERENCE TO RELATED APPLICATIONS

This application is a continuation-in-part of International Application No. PCT/US2015/50906, filed on Sep. 18, 2015, which designated the U.S., was published under PCT Article 21(2) in English, and claims priority under 35 U.S.C. § 119(e) to U.S. provisional patent application No. 62/052,111, filed on Sep. 18, 2014. The contents of all the related applications cross-referenced herein are herein incorporated by reference in their entirety as though fully set forth.

STATEMENT REGARDING FEDERALLY SPONSORED RESEARCH OR DEVELOPMENT

This invention was made with government support under Grant Nos. CA163200 and AA011999 awarded by the National Institutes of Health. The government has certain rights in the invention.

FIELD OF INVENTION

Provided herein are compositions and methods for treating, inhibiting, reducing the severity of and/or promoting prophylaxis of fibrosis, pancreatitis and/or pancreatic cancer in subject in need thereof. The compositions comprise inhibitors of IL-4/IL-13 receptor function.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Chronic pancreatitis (CP) is characterized by progressive and what is thought to be irreversible damage to the pancreas, with end result of endocrine and exocrine insufficiency. CP histologic features include chronic inflammation, fibrosis, acinar cell atrophy and distorted and/or blocked ducts. The management of CP is challenging with focus on the management of complications, and most patients remain symptomatic despite limited supportive therapy. Currently, there are no effective methods to limit progression or reverse this syndrome. Recurrent AP or pancreatic insults lead to necroinflammation and are linked to the development of pancreatic fibrosis (the necrosis-fibrosis concept). Recent in vitro and in vivo studies demonstrate the central role of activated pancreatic stellate cells (PSCs) in CP-associated fibrogenesis by regulating the synthesis and degradation of extracellular matrix proteins. PSCs are activated by many factors such as toxic factors associated with pancreatitis (for example, ethanol) and/or by cytokines released from injured acinar cells and/or pancreas-infiltrating leukocytes (such as macrophages and neutrophils).

Macrophages are innate immune cells, which are for simplicity divided into two spectra of major types based on Siamon Gordon's scheme: (1) classically activated macrophages (M1), induced by interferon gamma (IFNγ) and/or lipopolysaccharide, characterized by the production of reactive oxygen and nitrogen species and thought to play a critical role in host defense and antitumour immunity; and (2) alternatively activated macrophages (AAMs, M2), on exposure to IL-4/IL-13, are characterized by cell surface expression of scavenger receptors CD206. AAMs play key roles in dampening inflammation, promote wound-healing, fibrosis and tumorigenesis. Recent studies highlighted the function of macrophages as master regulators of fibrosis. Distinct macrophage populations contribute important activities towards the initiation, maintenance and resolution phase of fibrosis. Macrophages have been observed in dose proximity to PSCs in human pancreatic fibrosis, and their presence observed in rat model of CP, although not well defined, their potential role in CP has been suggested. Thus, the mechanism(s) by which crosstalk between activated stellate cells and macrophages trigger and sustain the fibrotic process during CP is not known. Delineating immune responses involved in the fibrotic processes will improve our understanding of disease pathogenesis and allow for designing novel therapeutics that can either treat and/or reverse the disease. Our study investigates and identifies macrophage characteristics and function in CP.

Herein, the inventors demonstrate that progression to CP is associated with alternative activation of macrophages and show an important role for the IL-4/IL-13 pathway in a crosstalk between macrophages and PSCs using in vivo and in vitro animal studies as well as ex vivo human primary cells. Notably, blocking IL-4/IL-13 using a peptide antagonist we show a therapeutic effect in established experimental CP and proof-of-concept therapeutic ex vivo effect using human samples. These studies are likely to offer potential benefit in a disease for which currently no active therapeutic agent exists and as such the disease is deemed progressive and irreversible.

SUMMARY OF THE INVENTION

Provided herein are pharmaceutical compositions comprising and inhibitor of IL-4/IL-13 receptor and a pharmaceutically acceptable carrier/excipient. In various embodiments, the inhibitor comprises, consists of or consists essentially of CSRM53567 (as described in SEQ ID NO: 1) peptide, CSRM535671 (as described in SEQ ID NO: 2) peptide, CSRM535672 (as described in SEQ ID NO: 3) peptide or a combination thereof, as described herein.

In some embodiments, the peptide can be modified to extend the shelf life and/or bioavailability using one or more non-natural peptide bonds or amino acids or by attaching to the peptide functional groups such as, e.g., polyethylene glycol (PEG).

The composition may further comprise a carrier, such as a pharmaceutically acceptable carrier.

Provided herein are methods for treating, inhibiting, reducing the severity of and/or promoting prophylaxis of a disease-state in a subject in need thereof. The method includes providing a composition comprising an inhibitor of IL-4/IL-13 receptor and administering an effective amount of the composition to the subject so as to treat, inhibit, reduce the severity of and/or promote prophylaxis of the disease state. In exemplary embodiments, the disease-state is fibrosis and/or cancer. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human.

Also provided herein are methods for treating, inhibiting, reducing the severity of or promoting prophylaxis of fibrosis in a subject in need thereof. The methods include providing a composition comprising an inhibitor of IL-4/IL-13 receptor and administering an effective amount of the composition to the subject so as to treat, inhibit, reduce the severity of and/or promote prophylaxis of fibrosis. The methods for treating, inhibiting, reducing the severity of or promoting prophylaxis of fibrosis may further comprise prescribing and/or administering existing therapies for organ-specific fibrosis. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human. In one embodiment, fibrosis is pancreatic fibrosis. In another embodiment, fibrosis is lung fibrosis.

Further provided herein are methods for treating, inhibiting, reducing the severity of and/or preventing metastasis of cancer in a subject in need thereof. The methods include providing a composition comprising an inhibitor of IL-4/IL-13 receptor and administering an effective amount of the composition to the subject so as to treat, inhibit, reduce the severity of and/or prevent metastasis of cancer. The methods for treating, inhibiting, reducing the severity of and/or preventing metastasis of cancer may further comprise prescribing and/or administering existing therapies for specific types of cancer. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human. In some embodiments, the cancer is pancreatic cancer. In some embodiments, the cancer is lung cancer.

Also provided herein are methods for treating, inhibiting, reducing the severity of or promoting prophylaxis of pancreatitis in a subject in need thereof. The methods include providing a composition comprising an inhibitor of IL-4/IL-13 receptor and administering an effective amount of the composition to the subject so as to treat, inhibit, reduce the severity of and/or promote prophylaxix of pancreatitis in the subject. The methods for treating, inhibiting, reducing the severity of and/or promoting prophylaxis of pancreatitis may further comprise prescribing and/or administering existing therapies for pancreatitis. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human. In some embodiments, the cancer is pancreatic cancer.

Further provided herein are methods for treating, inhibiting, reducing the severity of and/or promoting prophylaxis of disease-states associated with IL-4/IL-13 receptor signaling. The methods include providing a composition comprising an inhibitor of IL-4/IL-13 receptor and administering an effective amount of the composition to the subject so as to treat, inhibit, reduce the severity of and/or promote prophylaxis of disease-states associated with IL-4/IL-13 receptor signaling. In exemplary embodiments, the disease-states include chronic pancreatitis, chronic inflammation, fibrosis, cancer or a combination thereof. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human.

Also provided herein are methods for treating, inhibiting, reducing the severity of or promoting prophylaxis of disease-states treatable by inhibiting IL-4/IL-13 receptor function. The methods include providing a composition comprising an inhibitor of IL-4/IL-13 receptor and administering an effective amount of the composition to the subject so as to treat, inhibit, reduce the severity of and/or promote prophylaxis of disease-states treatable by inhibiting IL-4/IL-13 receptor function. In exemplary embodiments, the disease-states include chronic pancreatitis, chronic inflammation, fibrosis, cancer or a combination thereof. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human.

BRIEF DESCRIPTION OF FIGURES

Exemplary embodiments are illustrated in the referenced figures. It is intended that the embodiments and figures disclosed herein are to be considered illustrative rather than restrictive.

FIG. 1A to FIG. 1C depict, in accordance with various embodiments of the present invention, that CSRM53567 reduces macrophages and fibrosis in chronic pancreatitis mouse model. FIG. 1A show the treatment strategy, FIG. 1B shows the effect of CSRM53567 macrophages as measured by FACS. FIG. 1C shows the effect of CSRM53567 on preventing pancreas shrinkage due to chronic pancreatitis mediated fibrosis.

FIG. 2A to FIG. 2E depict, in accordance with various embodiments of the present invention, that macrophages are increased in mouse and human CP. FIG. 2A shows a heat map of cytokine and chemokine expressions in the pancreas lysates from control (Con) and CP mice quantitated via the Luminex analysis. FIG. 2B. shows representative immunofluorescence images of the pancreas from control and CP mice stained with amylase (acinar cells), α-SMA and GFAP (PSCs), F4/80 (macrophages) and 4,6-diamidino-2-phenylindole (DAPI). Scale bars, 50 μm. FIG. 2C shows representative immunofluorescence images of the human pancreas from paired normal and CP tissue stained with amylase, α-SMA, CD68 (macrophages) and DAPI. Scale bars, 50 μm. In FIG. 2D pancreatic leukocytes were isolated from control and CP mice and analysed using flow cytometry for macrophage numbers, BrdU incorporation, Ki-67 expression (n>3 per group). In FIG. 2E $CCR2^{WT}CD45.1^{+}$ $CD45.2^{+}$ C57BL/6 mice were lethally irradiated and reconstituted with a 1:1 mixture of BM cells from $CCR2^{WT}CD45.1^{+}$ and $CCR2^{KO}CD45.2^{+}$ mice over 8 weeks. Mice were injected with caerulein to induce CP as described herein, and macrophages (gated on $CD11b^{+}F4/80^{+}$ without prior CD45.2 gating) were analysed using flow cytometry following pancreatic leukocyte isolation. Representative flow cytometry plots and bar graphs depicting the proportion of macrophages and BrdU incorporation originating from $CCR2^{WT}CD45.1^{+}$ (black line) versus from $CCR2^{KO}CD45.2^{+}$ (grey line) and CCR2 expression are shown. n=3 for each group; mean±s.e.m., ns, not significant (unpaired two-tailed Student's t-test).

FIG. 3A to FIG. 3D depict, in accordance with various embodiments of the present invention, that alternatively activated macrophages are dominant in mouse and human CP. In FIG. 3A pancreatic leukocytes from control and CP mice were isolated and sorted for $SSC-A^{low}CD11b^{+}$ monocytes/macrophages (five mice were pooled for each group).

Markers of alternatively and classically activated macrophages were assessed using quantitative PCR. Expression of the genes was normalized to their relative expression in control mice. In FIG. 3B expression of alternative activation markers (CD206, IL-10 and IL-4Rα) and classical activation markers (MHCII and TNFα) in pancreatic macrophages of indicated mice were monitored using flow cytometry. MFI, mean fluorescence intensity; data presented as mean±s.e.m. (unpaired two-tailed Student's t-test). FIG. 3C shows representative immunofluorescence images of mouse and human CP tissues co-stained with macrophage F4/80 (mouse) or CD68 (human), CD206 (M2 marker) and DAPI (nuclei). FIG. 3D shows representative immunofluorescence images of mouse and human CP tissues, co-stained with F4/80 or CD68, TNFα (M1 marker) and DAPI. Scale bars, 50 μm.

FIG. 4A to FIG. 4G depict, in accordance with various embodiments of the present invention, that mouse and human pancreatic stellate cells promote alternative macrophage polarization. In FIG. 4A, culture supernatants from primary PSCs isolated from CP mice were collected and quantitated via the Luminex analysis, cytokine data presented as a heat map. FIG. 4B shows analysis of macrophage activation-associated genes in BMDMs cocultured in the presence or absence of PSCs for 2 days. Bar graphs represent BMDM gene expression in the presence of PSCs relative to absence of PSCs (BMDMs alone). In FIG. 4C, BMDMs were cultured with PSC conditioned medium (PSC_CM) or control medium (Con) for 24 h, and expression of CD206, IL-10, IL-4Rα, MHCII and TNFα determined using flow cytometry. In FIG. 4D, BMDMs from WT or IL-4Rα$^{-/-}$ mice were cultured with PSC_CM or IL-4/IL-13 (as a positive control for alternative macrophage polarization) for 24 h, and the expression of CD206 was examined using flow cytometry. In FIG. 4E, mouse PSCs were cultured with TGFβ (5 ng ml$^{-1}$), PDGFβ (10 ng ml$^{-1}$) or controls for 6 h and indicated gene expression was determined using qPCR. Representative bar graphs show relative mRNA expression over control treatments. In FIG. 4F, culture supernatants from primary PSCs derived from PDAC pieces (nos 2, 4, 6), normal margin of patients with PDAC (nos 3 and 5) and normal pancreas (no. 1; patient with nonpancreatic tumour requiring partial resection of the pancreas) were collected and quantitated via the Luminex analysis. Data presented as a cytokine heat map expression. In FIG. 4G, monocyte-derived human macrophages were exposed to the conditioned medium from human PSCs (hPSC_CM) for 24 h. The expressions of CD206 and TNFα were examined using flow cytometry. *P<0.05, P<0.01, *P<0.001. Data presented as means±s.e.m. (unpaired two-tailed Student's t-test).

FIG. 5A to FIG. 5F depict, in accordance with various embodiments of the present invention, that global or myeloid-specific IL-4Rα deficiency is protective against CP. WT, IL-4/IL-13$^{-/-}$, IL-4Rα$^{-/-}$ and LysM$^{cre}$ IL-4Rα$^{flox/flox}$ mice were subjected to caerulein-induced CP. In FIG. 5A, relative pancreas weight (pancreas weight/body weight) are shown. n=6-7 per genotype, means±s.e.m., ***P<0.001, ns, not significant, P<0.05 considered significant (one-way analysis of variance (ANOVA), Tukey's post hoc test). In FIG. 5B, histologic feature of the pancreas from different genotypes of mice are shown using H&E and Trichrome staining. Scale bar, 200 μm. FIG. 5C and FIG. 5D show quantitative RT-PCR analysis of fibrosis-associated genes αSMA (α-SMA) and Col1α1 (Collagen1A1) in the pancreas of indicated mice is shown. Means±s.e.m. *P<0.05, **P<0.01, ns, not significant (one-way ANOVA, Tukey's post hoc test). FIG. 5E shows representative immunofluorescence images of the pancreas from each genotype of mice (co-stained with α-SMA, Collagen1A1 and DAPI). FIG. 5F shows flow cytometry analysis of pancreatic macrophages (CD11b$^+$F4/80$^+$) CD206 expression (WI) from different genotypes of mice is shown. Means±s.e.m., *P<0.05, **P<0.01, ns, not significant (one-way ANOVA, Tukey's post hoc test).

FIG. 6A to FIG. 6G depict, in accordance with various embodiments of the present invention, that IL-4/IL-13-blocking peptide ameliorates established CP. IL-4/IL-13-blocking peptide (IL4/13BP i.p., 50 μg per mouse, 5 days per week) was administrated to mice 2 weeks after starting CP induction and mice were killed as previous after 4 weeks of caerulein injections. FIG. 6A shows relative pancreas weight from Con and IL4/13BP-treated mice. n=8-9 per group, means±s.e.m. (unpaired two-tailed Student's t-test). FIG. 6B shows representative pancreas H&E and Trichrome staining. Scale bar, 200 μm. FIG. 6C shows representative immunofluorescence images of the pancreas from indicated mice (co-stained with α-SMA, Collagen1A1 and DAPI). Scale bar: 50 μm. FIG. 6D and FIG. 6E show RT-PCR analysis of α-SMA and Col1α1 (Collagen1A1) gene expression in the pancreas of indicated mice. Means±s.e.m. (unpaired two-tailed Student's t-test). FIG. 6F shows flow cytometry analysis of CD206 expression (MFI) by pancreatic macrophages (CD11b$^+$F4/80$^+$) isolated from indicated mice. Means±s.e.m. (unpaired two-tailed Student's t-test). In FIG. 6G human macrophages as above were cultured with control medium (Con), conditioned medium from hPSCs (hPSC_CM) or hPSC_CM pretreated with 1 μM IL4/13BP (hPSC_CM+BP) for 24 h. Expression of CD206 (% CD206$^+$ macrophages) was analysed using flow cytometry.

FIG. 8A: IL-4/IL-13 blocking peptide enhances the response to radiation therapy; FIG. 8B: IL-4/IL-13 blocking peptide enhances the number of CD8+ T cells post-radiation therapy.

DETAILED DESCRIPTION OF THE INVENTION

Figure 2A:
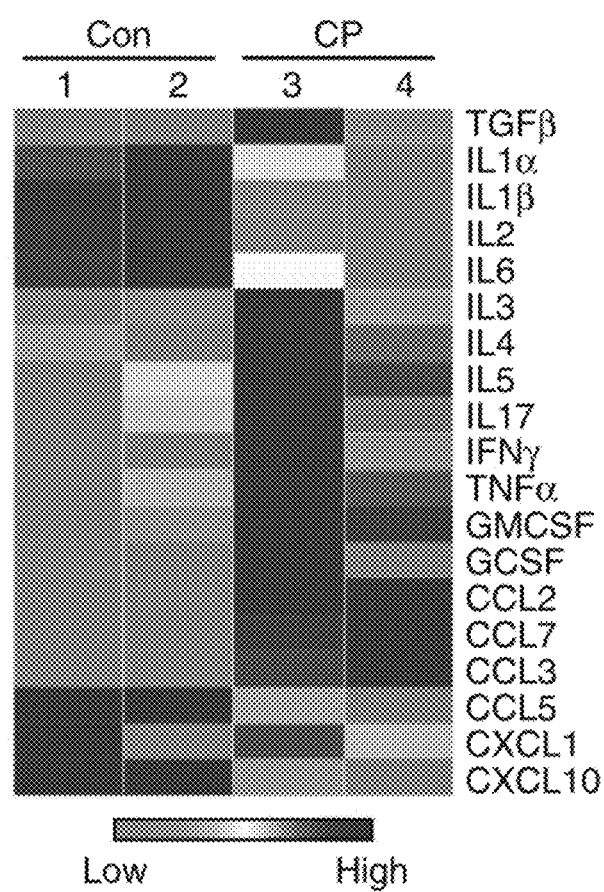

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed, revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 Jul., 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

For references on pediatrics, see Schwartz et al., The 5-Minute Pediatric Consult 4$^{th}$ ed., Lippincott Williams & Wilkins, (Jun. 16, 2005); Robertson et al., *The Harriet Lane*Handbook: A Manual for Pediatric House Officers 17$^{th}$ ed., Mosby (Jun. 24, 2005); and Hay et al., *Current Diagnosis and Treatment in Pediatrics* (*Current Pediatrics Diagnosis & Treatment*) 18$^{th}$ ed., McGraw-Hill Medical (Sep. 25, 2006).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. Beneficial or desired clinical results include, but are not limited to, alleviation of one or more symptom(s), diminishment of extent of the deficit, stabilized (i.e., not worsening) state of cancer progression, delay or slowing of metastasis or invasiveness, and amelioration or palliation of symptoms associated with the cancer. Treatment also includes a decrease in mortality or an increase in the lifespan of a subject as compared to one not receiving the treatment.

As used herein, the term "administering," refers to the placement an agent as disclosed herein into a subject by a method or route which results in at least partial localization of the agents at a desired site.

"A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. As used herein, the term "carcinoma" refers to a cancer arising from epithelial cells. As used herein, the term "invasive" refers to the ability to infiltrate and destroy surrounding tissue. Melanoma is an invasive form of skin tumor. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

The term "effective amount" as used herein refers to the amount of a pharmaceutical composition comprising one or more peptides as disclosed herein or a mutant, variant, analog or derivative thereof, to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the peptide. Measured or measurable parameters include clinically detectable markers of disease, for example, elevated or depressed levels of a biological marker, as well as parameters related to a clinically accepted scale of symptoms or markers for fibrosis and/or inflammation. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. The term does not denote a particular age or sex. Thus, adult and newborn subjects, as well as fetuses, whether male or female, are intended to be included within the scope of this term.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder, such as fibrosis, an autoimmune disease, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to fibrosis, chronic pancreatitis, cancer and/or any disease-state associated with IL-4/IL-13 receptor mediated function and/or signaling.

"Peptidomimetic" as used herein is a small protein-like chain designed to mimic a protein function. They may be modifications of an existing peptide or newly designed to mimic known peptides. They may be, for example peptoids and/or β-peptides and/or D-peptides.

"Recombinant virus" refers to a virus that has been genetically altered (e.g., by the addition or insertion of a heterologous nucleic acid construct into the particle).

A "gene" or "coding sequence" or a sequence which "encodes" a particular protein or peptide is a nucleic acid molecule that is transcribed (in the case of DNA) and translated (in the case of mRNA) into a polypeptide in vitro or in vivo when placed under the control of appropriate regulatory sequences. The boundaries of the gene are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346. Examples of well-known vehicles for gene transfer include adenovirus and recombinant adenovirus (RAd), adeno-associated virus (AAV), herpes simplex virus type 1 (HSV-1), and lentivirus (LV).

"Genetically modified cells", "genetically engineered cells", or "modified cells" as used herein refer to cells that express the polynucleotide having the sequence of any one or more of CSRM53567, CSRM535671, CSRM535672 or a combination thereof, or a variant, derivative, pharmaceutical equivalent, peptidomimetic or an analog thereof.

"Naked DNA" as used herein refers to DNA encoding a polypeptide having the sequence of any one or more of CSRM53567, CSRM535671, CSRM535672 or a combination thereof, or a variant, derivative, pharmaceutical equivalent, peptidomimetic or an analog thereof, cloned in a suitable expression vector in proper orientation for expression. Viral vectors which may be used include but are not limited SIN lentiviral vectors, retroviral vectors, foamy virus vectors, adeno-associated virus (AAV) vectors, hybrid vectors and/or plasmid transposons (for example sleeping beauty transposon system) or integrase based vector systems. Other vectors that may be used in connection with alternate embodiments of the invention will be apparent to those of skill in the art.

"Polynucleotide" as used herein includes but is not limited to DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. Virology, 52:456 (1973); Sambrook et al. *Molecular Cloning, a laboratory manual*, Cold Spring Harbor Laboratories, New York (1989); Davis et al., *Basic Methods in Molecular Biology*, Elsevier (1986), and Chu et al. *Gene* 13:197 (1981). Such techniques can be used to introduce one or more exogenous DNA moieties, such as a plasmid vector and other nucleic acid molecules, into suitable host cells. The term refers to both stable and transient uptake of the genetic material.

"Vector", "cloning vector" and "expression vector" as used herein refer to the vehicle by which a polynucleotide sequence (e.g. a foreign gene) can be introduced into a host cell, so as to transform the host and promote expression (e.g. transcription and translation) of the introduced sequence. Vectors include plasmids, phages, viruses, etc.

To date, there are no small molecule agents that target both IL-4/IL-13 cytokine pathways. Provided herein are IL4/IL-13 receptor inhibitors (for example small molecule inhibitors CSRM53567, CSRM535671 and CSRM535672) for prevention and/or treatment of fibrosis and/or cancer, for example, fibrosis in subjects with pancreatitis and pancreatic cancer.

Inhibitors

Provided herein are pharmaceutical compositions comprising, consisting of or consisting essentially of, an inhibitor that targets the IL-4/IL-13 receptor function and an acceptable carrier/excipient. In various embodiments, the inhibitor is any one or more of a small molecule, a peptide, a protein, an aptamer, an antibody or a fragment thereof, a nucleic acid molecule, a bispecific polypeptide comprising binding sites specific for IL-4 and the IL-4/IL-13 receptor, a bispecific polypeptide comprising binding sites specific for IL-13 and the IL-4/IL-13 receptor or a combination thereof.

In some embodiments, the inhibitors include but are not limited to, antibodies ("antibodies" includes antigen-binding portions of antibodies such as epitope or antigen-binding peptides, paratopes, functional CDRs; recombinant antibodies; chimeric antibodies; tribodies; midibodies; or antigen-binding derivatives, analogs, variants, portions, or fragments thereof), protein-binding agents, small molecules, recombinant protein, peptides, aptamers, avimers and protein-binding derivatives, portions or fragments thereof.

Also provided herein are pharmaceutical compositions comprising, consisting of or consisting essentially of an inhibitor that targets the IL-4/IL-13 receptor function and an acceptable carrier/excipient. In various embodiments, the inhibitor is any one or more of CSRM53567 peptide, CSRM535671 peptide, CSRM535672 peptide or combinations thereof, or analogs, pharmaceutical equivalents and/or peptidomimetics thereof, as described herein. In certain aspects of all the embodiments of the invention, the peptide further comprises a fusion protein. Specifically the fusion protein can be selected from an epitope tag and a half-life extender or a combination thereof. In certain embodiments, the one or more peptide causes a 10%, 20%, 30%, 40%, 50%, 60%, 70%, 80%, 90% 95% Or 100% inhibition of IL-4/IL-13 receptor function. When administered therapeutically, the peptide composition typically further comprises a pharmaceutically acceptable solution or carrier. In some aspects, the polypeptide or protein (for example, CSRM53567 peptide, CSRM535671 peptide, CSRM535672 peptide or combinations thereof) is a "modified polypeptide" comprising non-naturally occurring amino acids. In some aspects, the polypeptides comprise a combination of naturally occurring and non-naturally occurring amino acids, and in some embodiments, the peptides comprise only non-naturally occurring amino acids.

In one embodiment, the inhibitor is CSRM53567 comprising, consisting of or consisting essentially of the amino acid sequence TYR-CYS-ASP-ASP-PHE-VAL-GLY-SER-PHE-ASP-CYS-TYR (SEQ ID NO: 1), or an analog, pharmaceutical equivalent or a peptidomimetic thereof.

In another embodiment, the inhibitor is CSRM535671 comprising, consisting of or consisting essentially of the amino acid sequence TYR-CYS-ASP-ASP-PHE-VAL-GLY-SER-PHE-ASP-CYS-TYR-ASP (SEQ ID NO: 2), or an analog, pharmaceutical equivalent or a peptidomimetic thereof.

In a further embodiment, the inhibitor is CSRM535672 comprising, consisting of or consisting essentially of the amino acid sequence TYR-CYS-ASP-ASP-PHE-VAL-GLY-SER-PHE-ASP-CYS-TYR-GLU (SEQ ID NO: 3), or an analog, pharmaceutical equivalent or a peptidomimetic thereof.

In some embodiments, the inhibitors CSRM53567 peptide, CSRM535671 peptide, CSRM535672 peptide or combinations thereof, or analogs, pharmaceutical equivalents and/or peptidomimetics thereof are modified peptides. "Modified peptide" may include the incorporation of lactam-bridge, head-to-tail cyclization, non-natural amino acids into the peptides of the invention, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permeant complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. Therefore, in some embodiments the peptides as disclosed comprise L and D amino acids, wherein no more than 1, 2, 3, 4, 5, 6, 7, 8, 9, or 10 D-amino acids are included. In certain aspects, the peptides comprise more than 10 D-amino acids, and in certain aspects all the amino acids of the peptides are D-amino acids.

In some embodiments, the inhibitors are retro-inverso peptides of CSRM53567 peptide, CSRM535671 peptide, CSRM535672 peptide or combinations thereof, or analogs, pharmaceutical equivalents and/or peptidomimetics thereof. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A and Viscomi, G. C, J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

Other variants of the peptides described herein (for example, CSRM53567, CSRM535671, CSRM535672) can comprise conservatively substituted sequences, meaning that one or more amino acid residues of an original peptide are replaced by different residues, and that the conservatively substituted peptide retains a desired biological activity, i.e., the ability to inhibit the IL-4/IL-13 receptor that is essentially equivalent to that of the original peptide. Examples of conservative substitutions include substitution of amino acids that do not alter the secondary and/or tertiary structure of CSRM53567, CSRM535671, CSRM535672, substitutions that do not change the overall or local hydrophobic character, substitutions that do not change the overall or local charge, substitutions by residues of equivalent sidechain size, or substitutions by sidechains with similar reactive groups.

Other examples involve substitution of amino acids that have not been evolutionarily conserved in the parent sequence across species. Advantageously, in some embodiments, these conserved amino acids and structures are not altered when generating conservatively substituted sequences.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar sidechain volume are well known. Isolated peptides comprising conservative amino acid substitutions can be tested in any one of the assays described herein to confirm that a desired activity, e.g. inhibition of the IL-4/IL-13 receptor function is retained, as determined by the assays described elsewhere herein.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class.

Particularly preferred conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

Any cysteine residue not involved in maintaining the proper conformation of the isolated peptide as described herein can also be substituted, generally with serine, to improve the oxidative stability of the molecule and prevent aberrant crosslinking. Conversely, cysteine bond(s) can be added to the isolated peptide as described herein to improve its stability or facilitate multimerization.

As used herein, a "functional fragment" is a fragment or segment of a peptide comprising at least 5 amino acids and which can inhibit the IL-4/IL-13 receptor function according to the assays described herein. A functional fragment can comprise conservative substitutions of the sequences disclosed herein so long as they preserve the function of inhibiting the IL-4/IL-13 receptor function. This can be tested by detecting an inhibition of at least 50% of that of the parent (e.g. original) version of the peptide.

To enhance stability, bioavailability, and/or delivery of the peptides into the cells, the peptides can be modified. For example, in some embodiments, an isolated peptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, an isolated peptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, an isolated peptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, an isolated peptide can be modified, e.g. a moiety can be added to one or more of the amino acids comprising the peptide. In some embodiments, an isolated peptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, an isolated peptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties.

An isolated peptide as described herein can be coupled and or connected to a second functional molecule, peptide and/or polypeptide. In some embodiments, an isolated peptide as described herein is coupled to a targeting molecule. In some embodiments, an isolated peptide as described herein is coupled to a targeting molecule by expressing the peptide and the targeting molecule as a fusion peptide, optionally with a peptide linker sequence interposed between them. As used herein a "targeting molecule" can be any molecule, e.g. a peptide, antibody or fragment thereof, antigen, targeted liposome, or a small molecule that can bind to or be bound by a specific cell or tissue type. By way of non-limiting example, if it is desired to target an isolated peptide as described herein to the lung (e.g. to treat inflammation, lung fibrosis, or lung cancer), an isolated peptide comprising the amino acid sequence of any of SEQ ID NO: 1, SEQ ID NO: 2 or SEQ ID NO: 3 could be coupled to an antibody or fragment thereof which is specific for lung cells or tissue, e.g. an antibody or antibody fragment as described in US Patent Publication 2005/0287066. By way of non-limiting example, if it is desired to target an isolated peptide as described herein to the pancreas (e.g. to treat inflammation, pancreatic fibrosis, pancreatic cancer), an isolated peptide comprising the amino acid sequence of any of SEQ ID NO: 1, SEQ ID NO: 2 or SEQ ID NO: 3 could be coupled to an antibody or fragment thereof which is specific for lung cells or tissue, e.g. an antibody or antibody fragment that targets the ErbB receptors or and/or carcinoembryonic antigen (CEA) and/or Cancer antigen 19-9 (CA 19-9).

In some embodiments, an isolated peptide as described herein can be a fusion peptide or polypeptide. A fusion polypeptide can comprise a peptide linker domain interposed between the first domain of the peptide comprising an amino acid sequence of SEQ ID NOs: 1-3 or derivatives, variants, functional fragments, prodrug, or analog thereof as described herein and at least a second domain of the fusion peptide. The first peptide domain can be the N-terminal domain or the C-terminal domain or an internal sequence in the case where the partner domain forms after fragment complementation of constituent parts. Methods of synthesizing or producing a fusion protein are well known to those of ordinary skill in the art. The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. Fusion proteins can include an epitope tag or a half-life extender. Epitope tags include biotin, FLAG tag, c-myc, hemaglutinin, His6, digoxigenin, FITC, Cy3, Cy5, green fluorescent protein, V5 epitope tags, GST, β-galactosidase, AU1, AU5, and avidin. Half-life extenders include Fc domain and serum albumin.

In some embodiments, an isolated peptide as described herein can be a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. Progress in Drug Research 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design*. 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics,"

Pharm. Biotech. 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); B al imane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.,* 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.,* 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Prodrug, molecular structure and percutaneous delivery", *Des. Biopharm. Prop. Prodrugs Analogs,* [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", Adv. *Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), which are incorporated by reference herein in their entireties.

In some embodiments, an isolated peptide as described herein can be a pharmaceutically acceptable solvate. The term "solvate" refers to an isolated peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

In some embodiments, an isolated peptide as described herein can be in a non-crystalline, i.e. amorphous solid form.

In one aspect, described herein is a vector comprising a nucleic acid encoding a peptide as described herein. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc. Many vectors useful for transferring exogenous genes into target mammalian cells are available. The vectors can be episomal, e.g., plasmids, virus derived vectors such cytomegalovirus, adenovirus, etc., or can be integrated into the target cell genome, through homologous recombination or random integration, e.g., retrovirus derived vectors such MMLV, HIV-1, ALV, etc. Many viral vectors are known in the art and can be used as carriers of a nucleic acid modulatory compound into the cell. For example, constructs containing the nucleic acid encoding a polypeptide can be integrated and packaged into non-replicating, defective viral genomes like Adenovirus, Adeno-associated virus (AAV), or Herpes simplex virus (HSV) or others, including retroviral and lentiviral vectors, for infection or transduction into cells. Alternatively, the construct can be incorporated into vectors capable of episomal replication, e.g. EPV and EBV vectors. The nucleic acid incorporated into the vector can be operatively linked to an expression control sequence such that the expression control sequence controls and regulates the transcription and translation of that polynucleotide sequence.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector can comprise additional elements, for example, the expression vector can have two replication systems, thus allowing it to be maintained in two organisms, for example in human cells for expression and in a prokaryotic host for cloning and amplification.

The term "transfection" as used herein to methods, such as chemical methods, to introduce exogenous nucleic acids, such as the nucleic acid sequences encoding a peptide as described herein into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to those that use cyclodextrin, polymers, liposomes, nanoparticles, cationic lipids or mixtures thereof (e.g., DOPA, Lipofectamine and UptiFectin), and cationic polymers, such as DEAE-dextran or polyethylenimine.

As used herein, the term "viral vector" refers to a nucleic acid vector construct that includes at least one element of viral origin and has the capacity to be packaged into a viral vector particle. The viral vector can contain the nucleic acid encoding a peptide as described herein in place of non-essential viral genes. The vector and/or particle can be utilized for the purpose of transferring any nucleic acids into cells either in vitro or in vivo. Numerous forms of viral vectors are known in the art. The term "replication incompetent" when used in reference to a viral vector means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins for packaging the virus) and viral particles cannot be formed in the patient's cells. The term "transduction" as used herein refers to the use of viral particles or viruses to introduce exogenous nucleic acids into a cell.

Retroviruses, such as lentiviruses, provide a convenient platform for delivery of nucleic acid sequences encoding an agent of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu and Pathak Pharmacological Reviews 2000 52:493-512; which are incorporated by reference herein in their entirety.

In some embodiments, a nucleotide sequence of interest is inserted into an adenovirus-based expression vector. Unlike retroviruses, which integrate into the host genome, adenoviruses persist extrachromosomally thus minimizing the risks associated with insertional mutagenesis (Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76). Adenoviral vectors have several advantages in gene therapy. They infect a wide variety of cells, have a broad host-range, exhibit high efficiencies of infectivity, direct expression of heterologous sequences at high levels, and achieve long-term expression of those sequences in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. For all these reasons vectors derived from human adenoviruses, in which at least the E1 region has been deleted and replaced by a gene of interest, have been used extensively for gene therapy experiments in the pre-clinical and clinical phase. Adenoviral vectors for use with the compositions and methods described herein can be derived from any of the various adenoviral serotypes, including, without limitation, any of the over 40 serotype strains of adenovirus, such as serotypes 2, 5, 12, 40, and 41. The adenoviral vectors of used in the methods described herein are generally replication-deficient and contain the sequence of interest under the control of a suitable promoter. For example, U.S. Pat. No. 6,048,551, incorporated herein by reference in its entirety, describes replication-deficient adenoviral vectors that include a human gene under the control of the Rous Sarcoma Virus (RSV) promoter. Other recombinant adenoviruses of various serotypes, and comprising different promoter systems, can be created by those skilled in the art. See, e.g., U.S. Pat. No. 6,306,652, incorporated herein by reference in its entirety. Other useful adenovirus-based vectors for delivery of nucleic acid sequences include, but are not limited to: "minimal" adenovirus vectors as described in U.S. Pat. No. 6,306,652, which retain at least a portion of the viral genome required for encapsidation (the encapsidation signal), as well as at least one copy of at least a functional part or a derivative of the ITR; and the "gutless" (helper-dependent) adenovirus in which the vast majority of the viral genome has been removed and which produce essentially no viral proteins, such vectors can permit gene expression to persist for over a year after a single administration (Wu et al. (2001) Anesthes. 94:1119-32; Parks (2000) Clin. Genet. 58:1-11; Tsai et al. (2000) Curr. Opin. Mol. Ther. 2:515-23).

In some embodiments, a nucleotide sequence encoding a peptide as described herein is inserted into an adeno-associated virus-based expression vector. AAV is a parvovirus which belongs to the genus Dependovirus and has several features not found in other viruses. AAV can infect a wide range of host cells, including non-dividing cells. AAV can infect cells from different species. AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions, facilitating production, storage and transportation. AAV is a helper-dependent virus; that is, it requires co-infection with a helper virus (e.g., adenovirus, herpesvirus or vaccinia) in order to form AAV virions in the wild. In the absence of co-infection with a helper virus, AAV establishes a latent state in which the viral genome inserts into a host cell chromosome, but infectious virions are not produced. Subsequent infection by a helper virus rescues the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus. Adeno-associated virus (AAV) has been used with success in gene therapy. AAV has been engineered to deliver genes of interest by deleting the internal nonrepeating portion of the AAV genome (i.e., the rep and cap genes) and inserting a heterologous sequence (in this case, the sequence encoding the agent) between the ITRs. The heterologous sequence is typically functionally linked to a heterologous promoter (constitutive, cell-specific, or inducible) capable of driving expression in the patient's target cells under appropriate conditions. Recombinant AAV virions comprising a nucleic acid sequence encoding an agent of interest can be produced using a variety of art-recognized techniques, as described in U.S. Pat. Nos. 5,139,941; 5,622,856; 5,139,941; 6,001,650; and 6,004,797, the contents of each of which are incorporated by reference herein in their entireties. Vectors and cell lines necessary for preparing helper virus-free rAAV stocks are commercially available as the AAV Helper-Free System (Catalog No. 240071) (Agilent Technologies, Santa Clara, Calif.).

Additional viral vectors useful for delivering nucleic acid molecules encoding a peptide as described herein include those derived from the pox family of viruses, including vaccinia virus and avian poxvirus. Alternatively, avipoxviruses, such as the fowlpox and canarypox viruses, can be used to deliver the genes. The use of avipox vectors in cells of human and other mammalian species is advantageous with regard to safety because members of the avipox genus can only productively replicate in susceptible avian species. Methods for producing recombinant avipoxviruses are known in the art and employ genetic recombination, see, e.g., WO 91/12882; WO 89/03429; and WO 92/03545.

Molecular conjugate vectors, such as the adenovirus chimeric vectors, can also be used for delivery of sequence encoding a peptide as described herein (Michael et al. (1993) J. Biol. Chem. 268:6866-69 and Wagner et al. (1992) Proc. Natl. Acad. Sci. USA 89:6099-6103). Members of the Alphavirus genus, for example the Sindbis and Semliki Forest viruses, can also be used as viral vectors for delivering a nucleic acid sequence (See, e.g., Dubensky et al. (1996) J. Virol. 70:508-19; WO 95/07995; WO 96/17072).

In some embodiments, the vector further comprises a signal peptide operably linked to the peptide. Signal peptides are terminally (usually N-terminally) located peptide sequences that provide for passage of the protein into or through a membrane. Different signal peptides can be of use in different applications. For example, as regards a cellular system for the production of isolated peptides as described herein, a secretory signal peptide can permit increased yields and ease of purification. As a further example, as regards cells which produce peptides as described herein and which are administered for therapeutic purposes to a subject, multiple signal peptides, e.g. a peptide signaling for secretion from the first cell, a peptide signaling for internalization by a second cell, and a final peptide signaling for nuclear localization can increase the amount of peptide reaching the target environment. As a further example, as regards, e.g. gene therapy applications, a peptide signaling for nuclear localization can increase the amount of peptide reaching the target environment. Signal peptides are known in the art. Non-limiting examples of nuclear localization signal (NLS) peptides for use in mammalian cells include; the SV40 large T-antigen NLS (PKKKRKV) (SEQ ID NO: 4); the nucleoplasmin NLS (KR[PAATKKAGQA]KKKK)(SEQ ID NO: 5); the K-K/R-X-K/R (SEQ ID NO: 6) consensus NLS (KKXR (SEQ ID NO: 56); KKXK (SEQ ID NO: 57); KRXK (SEQ ID NO: 58); KRXR (SEQ ID NO: 59); and PY-NLSs (see, e.g. Dingwall et al. J Cell Biol 188 107:841-9 and Makkerh et al. Curr Biol. 1996 6:1025-7; both of which are incorporated by reference herein in their entireties, for further discussion). Non-limiting examples of secretion signal peptides for use in mammalian cells include human albumin signal peptide (MKWVTFISLLFLFSSAYS) (SEQ ID NO: 7); human chymotrypsin signal peptide (MAFLWLLSCWALLGTTGF) (SEQ ID NO: 8); human interleukin-2 signal peptide (MQLLSCIALILALV) (SEQ ID NO: 9); human trypsinogen-2 signal peptide (MNLLLILTFVAAAVA) (SEQ ID NO: 10); and sequences which include a coding region for a signal for precursor cleavage by signal peptidase, furin or other prohormone convertases (e.g., PC3). For example, a signal (peptide) sequence which is cleaved by furin (also known as PACE, see U.S. Pat. No. 5,460,950), other subtilisins (including PC2, PC1/PC3, PACE4, PC4, PC5/PC6, LPC/PC7IPC8/SPC7 and SKI-I; Nakayama, Biochem. J., 327:625-635 (1997)); enterokinase (see U.S. Pat. No. 5,270,181) or chymotrypsin can be introduced into the signal (peptide) sequence as defined herein. Additional signal peptides are known in the art and the choice of signal peptide can be influenced by the cell type, growth conditions, and the desired destination of the peptide.

In one aspect, described herein is a cell expressing a vector comprising a nucleic acid econding a peptide as described herein. In some embodiments, the cell expressing a vector as described herein is a cell suitable for the production of polypeptides. A cell suitable for the production of polypeptides can be a prokaryotic or eukaryotic cell, e.g. bacteria, virus, yeast, fungi, mammalian cells, insect cells, plant cells, and the like. By way of non-limiting example, cells for the production of proteins are commercially available, e.g. bacterial cells (BL21 derived cells—Cat. No. 60401-1, Lucigen; Middleton, Wis. and mammalian cells (293 F cells—Cat. No. 11625-019, Invitrogen; Grand Island, N.Y.).

Recombinant molecules, e.g. vectors as described herein, can be introduced into cells via transformation, particularly transduction, conjugation, lipofection, protoplast fusion, mobilization, particle bombardment, electroporation (Neumann et al., "Gene Transfer into Mouse Lyoma Cells by Electroporation in High Electric Fields," *EMBO J.* 1(7):841-845 (1982); Wong et al., "Electric Field Mediated Gene Transfer," *Biochem Biophys Res Commun* 107(2):584-587 (1982); Potter et al., "Enhancer-dependent Expression of Human Kappa Immunoglobulin Genes Introduced into Mouse pre-B Lymphocytes by Electroporation," *Proc. Natl. Acad. Sci. USA* 81(22):7161-7165 (1984), which are hereby incorporated by reference in their entirety), polyethylene glycol-mediated DNA uptake (Joseph Sambrook & David W. Russell, Molecular Cloning: A Laboratory Manual cp. 16 (2d ed. 1989), which is hereby incorporated by reference in its entirety), or fusion of protoplasts with other entities (e.g., minicells, cells, lysosomes, or other fusible lipid-surfaced bodies that contain the chimeric gene) (Fraley et al., "Liposome-mediated Delivery of Tobacco Mosaic Virus RNA into Tobacco Protoplasts: A Sensitive Assay for Monitoring Liposome-protoplast Interactions," *Proc. Natl. Acad. Sci. USA,* 79(6):1859-1863 (1982), which is hereby incorporated by reference in its entirety). The host cell is then cultured in a suitable medium, and under conditions suitable for expression of the protein or polypeptide of interest. After cultivation, the cell is disrupted by physical or chemical means, and the protein or polypeptide purified from the resultant crude extract. Alternatively, cultivation may include conditions in which the protein or polypeptide is secreted into the growth medium of the recombinant host cell, and the protein or polypeptide is isolated from the growth medium. Alternative methods may be used as suitable.

The peptides can also be attached to adjuvants. The term "adjuvant" refers to a compound or mixture that enhances the immune response and/or promotes the proper rate of absorption following inoculation, and, as used herein, encompasses any uptake-facilitating agent. Non-limiting examples of adjuvants include, chemokines (e.g., defensins, HCC-1, HCC4, MCP-1, MCP-3, MCP4, MIP-1α, MIP-1β, MIP-1δ, MIP-3α, MIP-2, RANTES); other ligands of chemokine receptors (e.g., CCR1, CCR-2, CCR-5, CCR6, CXCR-1); cytokines (e.g., IL-1β, IL-2, IL-4, IL-5, IL-6, IL-7, IL-8, IL-10, IL-12, IL-13, IL-15, IL-17 (A-F), IL-18; IFNα, IFN-γ; TNF-α; GM-CSF); TGF)-β; FLT-3 ligand; CD40 ligand; other ligands of receptors for those cytokines; Th1 cytokines including, without limitation, IFN-γ, IL-2, IL-12, IL-18, and TNF; Th2 cytokines including, without limitation, IL-4, IL-5, IL-10, and IL-13; and Th17 cytokines including, without limitation, IL-17 (A through F), IL-23, TGF-β and IL-6; immunostimulatory CpG motifs in bacterial DNA or oligonucleotides; derivatives of lipopolysaccharides such as monophosphoryl lipid A (MPL); muramyl dipeptide (MDP) and derivatives thereof (e.g., murabutide, threonyl-MDP, muramyl tripeptide, N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alani-ne-2-(1'-2'-dipalmitoyl-sn-glycero-3hydroxyphosphoryloxy)-ethylamine (CGP 19835A, referred to as MTP-PE)); MF59 (see Int'l Publication No. WO 90/14837); poly[di (carboxylatophenoxy)phosphazene] (PCPP polymer; Virus Research Institute, USA); RIBI (GSK), which contains three components extracted from bacteria, monophosphoryl lipid A, trehalose dimycolate and cell wall skeleton (MPL+ TDM+CWS) in a 2% squalene/Tween 80 emulsion; OM-174 (a glucosamine disaccharide related to lipid A; OM Pharma SA, Meyrin, Switzerland); heat shock proteins and derivatives thereof; Leishmania homologs of elF4a and derivatives thereof; bacterial ADP-ribosylating exotoxins and derivatives thereof (e.g., genetic mutants, A and/or B subunit-containing fragments, chemically toxoided versions); chemical conjugates or genetic recombinants containing bacterial ADP-ribosylating exotoxins or derivatives thereof; C3d tandem array; lipid A and derivatives thereof (e.g., monophosphoryl or diphosphoryl lipid A, lipid A analogs, AGP, AS02, AS04, DC-Chol, Detox, OM-174); ISCOMS and saponins (e.g., Quil A, QS-21, Stimulon® (Cambridge Bioscience, Worcester, Mass.)); squalene; superantigens; or salts (e.g., aluminum hydroxide or phosphate, calcium phosphate). See also Nohria et al. *Biotherapy*, 7:261-269, 1994; Richards et al., in *Vaccine Design*, Eds. Powell et al., Plenum Press, 1995; and Pashine et al., *Nature Medicine*, 11:S63-S68, 4/2005) for other useful adjuvants. Further examples of adjuvants can include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block co-polymer (CytRx, Atlanta Ga.), QS-21 (Cambridge Biotech Inc., Cambridge Mass.), and SAF-M (Chiron, Emeryville Calif.), AMPHIGEN® adjuvant, saponin, Quil A or other saponin fraction, monophosphoryl lipid A, and Avridine lipid-amine adjuvant, and METASTIM®. Other suitable adjuvants can include, for example, surface active substances such as lysolecithin, pluronic polyols, polyanions, peptides, oil or hydrocarbon emulsions, keyhole limpet hemocyanins, dinitrophenol, and others.

In some embodiment, cell may be genetically engineered to express the peptides described herein and the genetically engineered cells may be used for cell therapy. Examples of cells that may be used include but are not limited to, dendritic cells, T-lymphocytes (T-cells), naïve T cells ($T_N$), memory T cells (for example, central memory T cells ($T_{CM}$), effector memory cells ($T_{EM}$)), natural killer cells, hematopoietic stem cells and/or pluripotent embryonic/induced stem cells capable of giving rise to therapeutically relevant progeny. In an embodiment, the genetically engineered cells are autologous cells. By way of example, individual T-cells of the invention may be CD4+/CD8−, CD4−/CD8+, CD4−/CD8− or CD4+/CD8+. The T-cells may be a mixed population of CD4+/CD8− and CD4−/CD8+ cells or a population of a single clone. CD4+ T-cells may produce IL-2, IFNγ, TNFα and other T-cell effector cytokines when co-cultured in vitro with cells expressing the peptides (for example CD20+ and/or CD19+ tumor cells). $CD8^+$ T-cells may lyse antigen-specific target cells when co-cultured in vitro with the target cells. In some embodiments, T cells may be any one or more of $CD45RA^+$ $CD62L^+$ naïve cells, $CD45RO^+$ $CD62L^+$ central memory cells, $CD62L^-$ effector memory cells or a combination thereof (Berger et al., Adoptive transfer of virus-specific and tumor-specific T cell immunity. *Curr Opin Immunol* 2009 21(2)224-232).

In some embodiments, tolerized antigen presenting cells may be used in cell therapy. Examples include B cells, dendritic cells, macrophages and the like. The cells may be of any origin, including from humans. The cells may be tolerized using the peptides described herein. In some embodiments, the cell are tolerized in the presence of cytokines.

In some embodiments, the cell producing the peptide as described herein can be administered to a subject, e.g. for the treatment of pancreatic fibrosis, pancreatitis, pancreatic cancer, lung fibrosis or lung cancer.

In some embodiments, nanoparticles containing the peptide as described herein can be administrated to a subject. In some embodiments, the nanoparticles for use with the peptides described herein may be as described in Levine et al., Polymersomes: A new multi-functional tool for cancer diagnosis and therapy. *Methods* 2008 Vol 46 pg 25-32 or as described in S Jain, et al., Gold nanoparticles as novel agents for cancer therapy. *Br J Radiol.* 2012 February; 85(1010): 101-113.

In some embodiments, the cell expressing a vector encoding a peptide as described herein can be a cell of a subject, e.g. a subject administered gene therapy for the treatment of cancer. Vectors for gene therapy can comprise viral or non-viral vectors as described elsewhere herein.

Methods of Use

Provided herein are methods for treating, inhibiting, reducing the severity of and/or promoting prophylaxis of a disease-state in a subject in need thereof. The methods include providing a composition comprising an inhibitor of IL-4/IL-13 receptor and administering an effective amount of the composition to the subject so as to treat, inhibit, reduce the severity of and/or promote prophylaxis of the disease state. In various embodiments, the disease-state is fibrosis and/or cancer. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human. In various embodiments, the compositions described herein are administrated to the subject before, during, or after the subject develops the disease-state. In some embodiments, the composition is administrated to the subject 1-3 times per day or 1-7 times per week. In some embodiments, the composition is administrated to the subject for 1-5 days, 1-5 weeks, 1-5 months, or 1-5 years.

Provided herein are methods for treating, inhibiting, reducing the severity of or promoting prophylaxis of fibrosis (including chronic fibrosis) in a subject in need thereof. The methods include providing a composition comprising an inhibitor of IL-4/IL-13 receptor and administering an effective amount of the composition to the subject so as to treat, inhibit, reduce the severity of and/or promote prophylaxis of fibrosis. The methods for treating, inhibiting, reducing the severity of or promoting prophylaxis of fibrosis may further comprise administering existing therapies for organ-specific fibrosis.

In an exemplary embodiment, the methods for treating, inhibiting, reducing the severity of or promoting prophylaxis of fibrosis described herein may further comprise pharmacologic alleviation of abdominal pain, pharmacologic restoration of digestion and absorption, endoscopic treatments, surgical therapies, dietary care or combinations thereof for fibrosis in the pancreas.

In another exemplary embodiment, the methods for treating, inhibiting, reducing the severity of or promoting prophylaxis of fibrosis described herein may further comprise oxygen therapy, prednisone, azathioprine and/or N-acetylcysteine for lung fibrosis.

In an additional exemplary embodiment, the methods for treating, inhibiting, reducing the severity of or promoting prophylaxis of fibrosis may further comprise administering angiotensin converting enzyme inhibitor or Lisinopril for myocardial fibrosis.

The compositions described herein (for example compositions comprising CSRM53567, CSRM535671, CSRM535672 and/or a combination thereof, or analog, pharmaceutical equivalent or a peptidomimetic thereof) and existing therapies may be administered sequentially or simultaneously. In various embodiments of the methods described herein, fibrosis is any one or more of fibrosis of the pancreas, cystic fibrosis, mediastinal fibrosis, myelofibrosis, retroperitoneal fibrosis, progressive massive fibrosis, nephrogenic systemic fibrosis, Crohn's Disease, Keloid, Scleroderma/systemic sclerosis, Arthrofibrosis, Peyronie's disease, Dupuytren's contracture, adhesive capsulitis, fibrosis of the liver, fibrosis of the lung, fibrosis of the intestine, fibrosis of the heart, or combinations thereof.

Also provided herein are methods for treating, inhibiting, reducing the severity of or promoting prophylaxis of pancreatitis (such as chronic pancreatitis) in a subject in need thereof. The methods include providing a composition comprising an inhibitor of IL-4/IL-13 receptor and administering an effective amount of the composition to the subject so as to treat, inhibit, reduce the severity of and/or promote prophylaxix of pancreatitis in the subject. The methods for treating, inhibiting, reducing the severity of and/or promoting prophylaxis of pancreatitis may further comprise prescribing and/or administering existing therapies for pancreatitis. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human. In some embodiments, the cancer is pancreatic cancer. Examples of existing therapies include but are not limited to pharmacologic alleviation of abdominal pain, pharmacologic restoration of digestion and absorption, endoscopic treatments, surgical therapies, dietary care or combinations thereof. The compositions described herein (for example compositions comprising CSRM53567, CSRM535671, CSRM535672 and/or a combination thereof, or analog, pharmaceutical equivalent or a peptidomimetic thereof) and existing therapies may be administered sequentially or simultaneously.

Further provided herein are methods for treating, inhibiting, reducing the severity of and/or preventing metastasis of cancer in a subject in need thereof. The methods include providing a composition comprising an inhibitor of IL-4/IL-13 receptor and administering an effective amount of the composition to the subject so as to treat, inhibit, reduce the severity of and/or prevent metastasis of cancer. The methods for treating, inhibiting, reducing the severity of and/or preventing metastasis of cancer may further comprise prescribing and/or administering existing therapies for specific types of cancer, such as surgery, radiation therapy, or chemotherapy, or a combination thereof. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human. In some embodiments, the cancer is pancreatic cancer. In another embodiment, the cancer is breast cancer. The surgery, radiation therapy, or chemotherapy, or a combination thereof may be conducted before, during or after administering a therapeutically effective amount of the compositions described herein to the subject. In various embodiments of the methods described herein, the cancer is any one or more of lymphomas, sarcomas, brain cancer, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer Provided herein are methods for treating, inhibiting, reducing the severity of or promoting prophylaxis of disease-states associated with IL-4/IL-13 receptor signaling. The method includes providing a composition comprising an inhibitor of IL-4/IL-13 receptor and administering an effective amount of the composition to the subject so as to treat, inhibit, reduce the severity of and/or promote prophylaxis of disease-states associated with IL-4/IL-13 receptor signaling. In exemplary embodiments, the disease-states include chronic pancreatitis, chronic inflammation, fibrosis, cancer or a combination thereof. In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human.

Provided herein are methods for treating, inhibiting, reducing the severity of or promoting prophylaxis of disease-states treatable by inhibiting IL-4/IL-13 receptor function. The method includes providing a composition comprising an inhibitor of IL-4/IL-13 receptor and administering an effective amount of the composition to the subject so as to treat, inhibit, reduce the severity of and/or promote prophylaxis of disease-states treatable by inhibiting IL-4/IL-13 receptor function. In exemplary embodiments, the disease-states include chronic pancreatitis, chronic inflammation, fibrosis, cancer or a combination thereof. In some embodiments, the disease-state is cancer (for example, pancreatic cancer or breast cancer). In some embodiments, the inhibitor of IL-4/IL-13 receptor is any one or more of CSRM53567, CSRM535671, CSRM535672 and/or a combination thereof, or analog, pharmaceutical equivalent or a peptidomimetic thereof. In one embodiment, the subject is human.

In various embodiments of the pharmaceutical compositions and methods described herein, the compositions (for example, compositions comprising any one or more of CSRM53567, CSRM535671, CSRM535672 and/or a combination thereof, or analog, pharmaceutical equivalent or a peptidomimetic thereof), may be administered concurrently or sequentially with other therapeutic agents including but not limited to chemotherapeutic agents and/or radiation therapy.

In some embodiments, chemotherapeutic agents may be selected from any one or more of cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.).

In various embodiments, therapies include, for example, radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or tele-therapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments, therapies include, for example, immunotherapy. Immunotherapy may comprise, for example, use of cancer vaccines and/or sensitized antigen presenting cells. In some embodiments, therapies include targeting cells in the tumor microenvironment or targeting immune cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

In various embodiments, therapies include, for example, hormonal therapy, Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In various embodiments, the effective amount of the inhibitor of IL-4/IL-13 receptor (for example, any one or more of CSRM53567, CSRM535671, CSRM535672 and/or a combination thereof, or analog, pharmaceutical equivalent or a peptidomimetic thereof) is any one or more of about 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Typical dosages of an effective amount of the IL-4/IL-13 receptor inhibitor can be in the ranges recommended by the manufacturer where known therapeutic compounds are used, and also as indicated to the skilled artisan by the in vitro responses or responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, such as biopsied malignant tumors, or the responses observed in the appropriate animal models. In various embodiments, the compositions of the invention comprising the IL-4/IL-13 receptor inhibitor may be administered once a day (SID/QD), twice a day (BID), three times a day (TID), four times a day (QID), or more, so as to administer an effective amount of the IL-4/IL-13 receptor inhibitor to the subject, where the effective amount is any one or more of the doses described herein.

In various embodiments, the subject is selected from the group consisting of human, non-human primate, monkey, ape, dog, cat, cow, horse, rabbit, mouse and rat.

Methods for Producing IL-4/IL-13 Inhibitors

Provided herein are methods for producing any one or more of CSRM53567, CSRM535671, CSRM535672 or a combination thereof, or a variant, derivative, pharmaceutical equivalent, peptidomimetic or an analog thereof. The CSRM53567, CSRM535671, CSRM535672 or a combination thereof, or a variant, derivative, pharmaceutical equivalent, peptidomimetic or an analog thereof may be recombinant or chemically synthesized (Murali, R. and Green, M. *Pharmaceuticals* 2012 Vol 5 209-235). These may be modified by one or more purification tags, including, but not limited to, His6, epitope (e.g., myc, V5, FLAG or soft-epitope), streptavidin, biotin, avidin, tetracysteine, calmodulin-binding protein, elastin-like peptide, fusion protein (e.g., glutathione-S-transferase, maltose binding protein, cellulose-binding domain, thioredoxin, NusA or mistin), chitin-binding domain, GFP, alkaline phosphatase, cutinase, $O^6$-alkylguanine alkyltransferase (AGT), or halo tag. In one embodiment, CSRM53567 comprises, consists of or consists essentially of the amino acid sequence TYR-CYS-ASP-ASP-PHE-VAL-GLY-SER-PHE-ASP-CYS-TYR (SEQ ID NO: 1), or an analog, pharmaceutical equivalent or a peptidomimetic thereof. In another embodiment, CSRM535671 comprises, consists of or consists essentially of the amino acid sequence TYR-CYS-ASP-ASP-PHE-VAL-GLY-SER-PHE-ASP-CYS-TYR-ASP (SEQ ID NO: 2), or an analog, pharmaceutical equivalent or a peptidomimetic thereof. In a further embodiment, the inhibitor is CSRM535672 comprises, consists of or consists essentially of the amino acid sequence TYR-CYS-ASP-ASP-PHE-VAL-GLY-SER-PHE-ASP CYS-TYR-GLU (SEQ ID NO: 3), or an analog, pharmaceutical equivalent or a peptidomimetic thereof.

In some embodiments, the method involves growing the host-vector system transfected with a vectors encoding any one or more of CSRM53567, CSRM535671, CSRM535672 or a combination thereof, or a variant, derivative, pharmaceutical equivalent, peptidomimetic or an analog thereof, so as to produce the any one or more of CSRM53567, CSRM535671, CSRM535672 or a combination thereof, or a variant, derivative, pharmaceutical equivalent, peptidomimetic or an analog thereof, in the host cells and then recovering any one or more of CSRM53567, CSRM535671, CSRM535672 or a combination thereof, or a variant, derivative, pharmaceutical equivalent, peptidomimetic or an analog thereof. The techniques for assembling and expressing DNA encoding the amino acid sequences corresponding to any one or more of CSRM53567, CSRM535671, CSRM535672 or a combination thereof, or a variant, derivative, pharmaceutical equivalent, peptidomimetic or an analog thereof, e.g. synthesis of oligonucleotides, PCR, transforming cells, constructing vectors, expression systems, and the like are well-established in the art, and most practitioners are familiar with the standard resource materials for specific conditions and procedures. The nucleotide sequences encoding the amino acid sequences corresponding to any one or more of CSRM53567, CSRM535671, CSRM535672 or a combination thereof, or a variant, derivative, pharmaceutical equivalent, peptidomimetic or an analog thereof, may be expressed in a variety of systems known in the art. The cDNA may be excised by suitable restriction enzymes and ligated into suitable prokaryotic or eukaryotic expression vectors for such expression.

Specifically, construction of suitable vectors containing the desired gene coding and control sequences employs standard ligation and restriction techniques, which are well understood in the art (see Maniatis et al., in *Molecular Cloning*: A Laboratory Manual, Cold Spring Harbor Laboratory, New York (1982). Isolated plasmids, DNA sequences, or synthesized oligonucleotides are cleaved, tailored, and re-ligated in the form desired (*Methods in Enzymology* 65:499-560 (1980); D. Goeddel (ed.) Gene Expression Technology: Methods in Enzymology (1991).

The recombinant protein may be expressed in a prokaryotic, yeast, insect, plant or mammalian system. Examples of well-known prokaryotic (bacterial) expression systems are *E. coli* (e.g. BL21, BL21 (DE3), XL1, XL1 Blue, DH5α or DH10B cell strains) and *B. subtilis*. Yeast cells include, but are not limited to, *P. pastoris, K. lactis, S. cerevisiae, S. pombe, Y. lipolyt* and *K. marxianus*. Suitable mammalian cell lines may be, among others, CHO, HEK 293 BHK, NS0, NS1, SP2/0. Insect cell lines may include, for example, *Drosophila, Aedes aegypti* mosquitoe, Sf21, Sf9, and T.ni cell lines. The isolated protein may comprise, depending of the expression system, different posttranslational modifications of amino acids, such as acetate groups, phosphate groups, various lipids and carbohydrates, changed chemical nature of an amino acid (e.g. citrullination) or structural changes, like disulfide bridges.

Suitable vectors include but are not limited to viral vector systems e.g. self-inactivating (SIN) lentiviral vectors, retroviral vectors, foamy virus vectors, adeno virus vectors, adeno-associated virus (AAV) vectors, HSV-1 amplicons, replication-competent vectors (for example ONYX-015) and/or plasmid transposons (for example, sleeping beauty transposon vectors), ADV, RV (R. J. Kaufman "Vectors used for expression in mammalian cells" in *Gene Expression Technology*, edited by D. V. Goeddel (1991).

Many methods for inserting functional DNA transgenes into cells are known in the art. For example, non-vector methods include nonviral physical transfection of DNA into cells; for example, microinjection (DePamphilis et al., *BioTechnique* 6:662-680 (1988)); liposomal mediated transfection (Felgner et al., *Proc. Natl. Acad. Sci. USA*, 84:7413-7417 (1987), Felgner and Holm, *Focus* 11:21-25 (1989) and Felgner et al., *Proc. West. Pharmacol. Soc.* 32: 115-121 (1989)) and other methods known in the art.

Pharmaceutical Compositions

Provided herein are pharmaceutical compositions comprising, consisting of or consisting essentially of, an inhibitor that targets the IL-4/IL-13 receptor function and an acceptable carrier/excipeint. In various embodiments, the inhibitor is any one or more of CSRM53567, CSRM535671, CSRM535672 or a combination thereof, or an analog, pharmaceutical equivalent or a peptidomimetic thereof. In one embodiment, the inhibitor is CSRM53567 comprising, consisting of or consisting essentially of the amino acid sequence TYR-CYS-ASP-ASP-PHE-VAL-GLY-SER-PHE-ASP-CYS-TYR ((SEQ ID NO: 1), or an analog, pharmaceutical equivalent or a peptidomimetic thereof. In another embodiment, the inhibitor is CSRM535671 comprising, consisting of or consisting essentially of the sequence TYR-CYS-ASP-ASP-PHE-VAL-GLY-SER-PHE-ASP-CYS-TYR-ASP (SEQ ID NO: 2), or an analog, pharmaceutical equivalent or a peptidomimetic thereof. In another embodiment, the inhibitor is CSRM535672 comprising, consisting of or consisting essentially of the sequence TYR-CYS-ASP-ASP-PHE-VAL-GLY-SER-PHE-ASP-CYS-TYR-GLU (SEQ ID NO: 3), or an analog, pharmaceutical equivalent or a peptidomimetic thereof.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of inhibitors of IL-4/IL-13 receptor other than directly into a target site, tissue, or organ, such that it enters the subject's circulatory system and, thus, is subject to metabolism and other like processes.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. In various embodiments, the composition is administered to the subject 1-3 times per day or 1-7 times per week. In various embodiments, the composition is administered to the subject for 1-5 days, 1-5 weeks, 1-5 months, or 1-5 years. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity. While the attending physician ultimately will decide the appropriate amount and dosage regimen, therapeutically effective amounts of the one or more peptides as disclosed herein or a mutant, variant, analog or derivative thereof may be provided at a dose of 0.0001, 0.01, 0.01 0.1, 1, 5, 10, 25, 50, 100, 500, or 1,000 mg/kg or µg/kg. Effective doses may be extrapolated from dose-response curves derived from in vitro or animal model test bioassays or systems.

An effective amount as used herein would also include an amount sufficient to delay the development of a symptom of the disease, alter the course of a symptom of disease (for example but not limited to, slow the progression of a symptom of the disease), or reverse a symptom of disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent for inhibiting IL-4/IL-13 receptor function, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" or "pharmaceutically acceptable excipient" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an inhibitor of IL-4/IL-13 receptor. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (18) pH buffered solutions; (19) polyesters, polycarbonates and/or polyanhydrides; (20) bulking agents, such as polypeptides and amino acids (21) serum components, such as serum albumin, HDL and LDL; (22) C2-C12 alchols, such as ethanol; and (23) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The inhibitors of IL-4/IL-13 receptor described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (7) nasally. Additionally, the inhibitors of IL-4/IL-13 receptor described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 3,270,960.

Further embodiments of the formulations and modes of administration of inhibitors of IL-4/IL-13 receptor that can be used in the methods described herein are illustrated below.

Parenteral Dosage Forms. Parenteral dosage forms of inhibitors of IL-4/IL-13 receptor can also be administered to a subject by various routes, including, but not limited to, subcutaneous, intravenous (including bolus injection), intramuscular, and intra-arterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol formulations. Inhibitors of IL-4/IL-13 receptor can be packaged in a pressurized aerosol container together with suitable propellants, for example, hydrocarbon propellants like propane, butane, or isobutane with conventional adjuvants. Inhibitors of IL-4/IL-13 receptor can also be administered in a non-pressurized form such as in a nebulizer or atomizer. Inhibitors of IL-4/IL-13 receptor can also be administered directly to the airways in the form of a dry powder, for example, by use of an inhaler.

Suitable powder compositions include, by way of illustration, powdered preparations of inhibitors of IL-4/IL-13 receptor thoroughly intermixed with lactose, or other inert powders acceptable for intra-bronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the inhibitors of IL-4/IL-13 receptor described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms. In some embodiments of the methods described herein, inhibitors of IL-4/IL-13 receptor can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound's onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the inhibitors of IL-4/IL-13 receptor described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

In some embodiments, inhibitors of IL-4/IL-13 receptor for use in the methods described herein are administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of the inhibitors of IL-4/IL-13 receptor administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Kits of the Invention

The invention also provides a kit for the treatment of cancer and/or fibrosing disorder, inhibition of cancer and/or fibrosing disorder, reduction of cancer and/or fibrosing disorder or promotion of cancer and/or fibrosing disorder prophylaxis in a subject in need thereof. The kit comprises a composition comprising a IL-4/IL-13 receptor inhibitor and instructions for use of the composition for treating, inhibiting and/or reducing the severity of cancer and/or fibrosing disorder in subjects in need thereof. In some embodiments, the IL-4/IL-13 receptor inhibitor is a small molecule, a peptide, a protein, an aptamer, an antibody or a fragment thereof, a nucleic acid molecule or a bispecific polypeptide agent comprising binding sites specific for IL-4 or IL-13 and IL-4/IL-13 receptor. In various embodiments, the inhibitor is any one or more of CSRM53567, CSRM535671, CSRM535672 or a combination thereof, or an analog, pharmaceutical equivalent or a peptidomimetic thereof.

The kit is an assemblage of materials or components, including at least one of the compositions described herein. Thus, in some embodiments the kit contains a composition including a IL-4/IL-13 receptor inhibitor, wherein the IL-4/IL-13 receptor inhibitor is any one or more of CSRM53567, CSRM535671, CSRM535672 or a combination thereof, or an analog, pharmaceutical equivalent or a peptidomimetic thereof, as described herein.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat, reduce the severity of, inhibit or prevent cancer and/or fibrosing disorders in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing a the inhibitor is any one or more of CSRM53567, CSRM535671, CSRM535672 or a combination thereof, or an analog, pharmaceutical equivalent or a peptidomimetic thereof. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Provided herein is an inhibitor CSRM53567 designed to inhibit IL-4/IL-13 receptor function. We provide evidence of benefit of CSRM53567 in a model of chronic pancreatitis characterized by chronic inflammation and tissue fibrosis. Current knowledge about the role of IL-4/IL-13 receptors in the mechanisms of chronic inflammation and fibrosis and the role of these processes in cancers suggest that agents that inhibit IL-4/IL-13 receptors will have benefit in a broad group of chronic inflammatory/fibrosing diseases and cancers.

As examples, chronic pancreatitis and pancreatic cancer are characterized by tissue fibrosis caused by sustained pancreatic inflammation accompanied by fibrosis. Several lines of evidence suggest that myeloid cells, pancreatic stellate cells (PSCs) and pro-inflammatory cytokines from stellate cells and myeloid cells play central roles in disease pathogenesis. Stellate cells in the pancreas when activated during chronic pancreatitis and pancreatic cancer have similar characteristics and functions to fibroblastic cells in other tissue pathologies.

To date, there are no small molecule agents that target both IL-4/IL-13 cytokine pathways. Provided herein are IL-4/IL-13 receptor inhibitors, for example small molecule inhibitors CSRM53567, CSRM535671 and CSRM535672, for prevention and/or treatment of fibrosis in pancreatitis and pancreatic cancer.

Exemplary Inhibitors of IL-4/IL-13 Receptors:

```
CSRM53567:
                                   (SEQ ID NO: 1)
TYR-CYS-ASP-ASP-PHE-VAL-GLY-SER-PHE-ASP-CYS-TYR
(CYS2-CYS11 disulfide)

CSRM535671:
                                   (SEQ ID NO: 2)
TYR-CYS-ASP-ASP-PHE-VAL-GLY-SER-PHE-ASP-CYS-

TYR-ASP
(CYS2-CYS11 disulfide)

CSRM535672:
                                   (SEQ ID NO: 3)
TYR-CYS-ASP-ASP-PHE-VAL-GLY-SER-PHE-ASP-CYS-

TYR-GLU
(CYS2-CYS11 disulfide)
```

Preliminary results are shown in FIG. 1A-FIG. 1B. As indicated herein, agents that inhibit IL-4/IL-13 receptor function such as CRSM53567 will have benefit in several fibrosis and cancer diseases. Experimental design is shown in FIG. 1A. In this design a commonly used model to cause chronic pancreatitis in rodents was created. In this model, the animal is given the cholecystokinin analogue, Caerulein, as a set of 6 intraperitoneal injections over a day repeated 3 times a week for 4 weeks. FIG. 1B shows that CSRM53567 decreases macrophages in the tissue. CD206 is a marker of the type II macrophage while MHCII is highly expressed on type I macrophage. The increase in the tissue volume in CSRM53567 treated group is a reflection of decreased fibrosis (FIG. 1B).

Example 2

Experimental Methods

Mice: BALB/c, C57BL/6, SJL, B6, SJL, IL-4Rα$^{-/-}$, CCR2$^{KO}$ mouse strains were purchased from Jackson Laboratory and bred in-house. LysM$^{cre}$IL-4Rα$^{flox/flox}$ (ref. 24) and IL-4/IL-13$^{-/-}$ (McKenzie, G. J., et al. Simultaneous disruption of interleukin (IL)-4 and IL-13 defines individual roles in T helper cell type 2-mediated responses. *J. Exp. Med.* 189, 1565-1572 (1999)) mice on BALB/c background were generated as described. All experimental mice were age—(6-8 weeks) and sex-matched, and animal experiments were approved by the Stanford University institutional animal care and use committees.

Mixed bone marrow chimeras: Competitive mixed BM chimeric mice were generated by lethally irradiating CCR2$^{WT}$ CD45.1$^+$ CD45.2$^+$ C57BL/6 mice with 9.5-Gy γ radiation in two doses at ~3 h apart, followed' by i.v. injection of 5×10$^6$ BM cells comprising 1:1 mixture of cells from CCR2$^{WT}$CD45.1$^+$ and CCR2$^{KO}$CD45.2$^+$ mice. Chimeric mice were left to engraft for at least 8 weeks before further experimental manipulation.

Pancreatitis model and treatment: AP was induced with caerulein injection in mice as previously described (Xue, J., et al. Aryl hydrocarbon receptor regulates pancreatic IL-22 production and protects mice from acute pancreatitis. *Gastroenterology* 143, 1670-1680 (2012); Xue, J. & Habtezion, A. Carbon monoxide-based therapy ameliorates acute pancreatitis via TLR4 inhibition. *J. Clin. Invest.* 124, 437-447 (2014)). CP was induced by repetitive caerulein injections (Lerch, M. M. & Gorelick, F. S. Models of acute and chronic pancreatitis. *Gastroenterology* 144, 1180-1193 (2013); Treiber, M. et al. Myeloid, but not pancreatic, RelA/p65 is required for fibrosis in a mouse model of chronic pancreatitis. *Gastroenterology* 141, e1471-e1477 (2011)). In brief, mice were given six hourly intraperitoneal (i.p.) injections of 50-µg kg$^{-1}$ body weight caerulein (Sigma-Aldrich) 3 days per week, for a total of 4 weeks. Mice were then killed and analyzed 3 days after the last caerulein injection. For blocking peptide study all mice were given caerulein injection 3 days per week for a total of 4 weeks as above, and 2 weeks following start of the caerulein injection mice were either given vehicle control (PBS) or IL-4/IL-13-blocking peptide (50 µg per mouse, 100 µl daily for 5 days per week×2 weeks) until being killed 4 weeks and 3 days later as above.

Human samples: Human pancreatic tissues from patients with CP, pancreatic ductal adenocarcinoma (PDAC) and normal pancreas margins from patients with PDAC, and one from a patient with normal pancreas (patient had adjacent non-pancreatic tumor that required partial resection of the pancreas) were obtained from the Stanford tissue bank with Local Ethics Committee approval and patient consents.

Histology and immunofluorescence: Mice were killed by $CO_2$ inhalation, and then their pancreata were rapidly removed. Pancreas pieces were immediately fixed in 10% formalin or frozen in Tissue-Tek OCT compound. Fixed tissues were sectioned and used for haemotoxylin and eosin and Trichrome staining (performed in the Histo-Tec Laboratory). Frozen tissues were also sectioned for immunofluorescence staining with indicated antibodies and analyzed with confocal microscopy.

The Luminex assay: The assay was performed in the Human Immune Monitoring Center at Stanford University (Xue, J. & Habtezion, A. Carbon monoxide-based therapy ameliorates acute pancreatitis via TLR4 inhibition. *J. Clin. Invest.* 124, 437-447 (2014)). Human 63-plex or Mouse 26 plex kits were purchased from Affymetrix and used according to the manufacturer's recommendations with modifications as described below. Briefly, samples were mixed with antibody-linked polystyrene beads on 96-well filter-bottom plates and incubated at room temperature for 2 h followed by overnight incubation at 4° C. Room temperature incubation steps were performed on an orbital shaker at 500-600 r.p.m. Plates were vacuum-filtered and washed twice, and then incubated with biotinylated detection antibody for 2 h at room temperature. Samples were then filtered and washed twice as above and resuspended in streptavidin-phycoerythrin (PE). After incubation for 40 min at room temperature, two additional vacuum washes were performed and the samples resuspended in Reading Buffer. Each sample was measured in duplicate. Plates were read using a Luminex 200 instrument.

Antibodies and flow cytometry: All antibodies used for flow cytometry were purchased from Biolegend, unless indicated. For surface staining, murine cells were stained with the following antibodies: APC-CD45.2 (109814, 1:200), PE/Cy7-CD4 (100528, 1:300), Percp/Cy5.5-CD11b (101228, 1:200), BV421-F4/80 (123137, 1:200), APC/Cy7-CD11C (117324, 1:200), PE-IL-411.a (144803 1:100), AF488-CD206 (141710, 1:100), AF700-MHCII (107622, 1:300), PB-Ly6C (128014, 1:200), PE/Cy7-Ly-6G (127617, 1:300), PE-FcεRIα (134307, 1:200), AF488-ckit (105815, 1:200), APC-eFluor780-CD45.1 (47-0453-82, eBioscience, 1:200) and PE-Siglec-F (562068, BD Biosciences, 1:200). Human cells were stained with PE/Cy7-CD14 (301814, 1:100), AF488-CD206 (321114, 1:50) and APC-CD68 (333810, 1:100). For intracellular cytokine staining, cells were activated with phorbol myristate acetate (50 ng ml$^{-1}$) and ionomycin (1 µg ml$^{-1}$), in the presence of brefeldin A (10 µg ml$^{-1}$, eBioscience) for 4 h at 37° C. before staining. The cells were then fixed and permeabilized using the eBioscience kit following the manufacturer's guidelines. APC-IL10 (554468, 1:100) and isotype control (556924, 1:100) from BD Biosciences were used for intracellular staining. For intracellular TNFα staining, cells were incubated with or without lipopolysaccharide (100 ngml-1, InvivoGen) in the presence of brefeldin A before surface-staining. PE-TNFα (554419, 1:200) and isotype control (554685, 1:200) from BD Biosciences were used.

For detection of intracellular Ki-67 and BrdU, cells were stained for surface makers and then fixed and permeabilized using Foxp3 staining buffer set (eBioscience). For BrdU staining, cells were first incubated with DNase for 1 h at 37° C. The Cells were then stained with PE-BrdU (339812, 1:100) or AF488-Ki67 (558616, BD Biosciences, 1:50). Dead cells were excluded from analysis using violet viability stain (Invitrogen). Flow cytometry data collection was performed on Fortessa LSRII (BD Biosciences) and analysed using the FlowJo software (Tree Star Inc.).

Cell preparation and in vitro cultures: Pancreatic leukocytes were isolated using collagenase digestion method described previously for flow cytometry analysis (Xue, J., et al. Aryl hydrocarbon receptor regulates pancreatic IL-22 production and protects mice from acute pancreatitis. *Gastroenterology* 143, 1670-1680 (2012)). PSCs from CP mice were isolated by outgrowth method as described (Bachem, M. G. et al. Identification, culture, and characterization of pancreatic stellate cells in rats and humans. *Gastroenterology* 115, 421-432 (1998)). Primary human PSCs from normal margins and PDAC were isolated using gradient centrifugation and outgrowth method, respectively (Bachem, M. G. et al. Identification, culture, and characterization of pancreatic stellate cells in rats and humans. *Gastroenterology* 115, 421-432 (1998); Apte, M. V. et al. Periacinar stellate shaped cells in rat pancreas: identification, isolation, and culture. *Gut* 43, 128-133 (1998)). Murine PSCs were cultured in DMEM/F12 (1:1) medium containing 10% FBS. Where indicated, mouse PSCs were cultured with TGFβ (5 ng ml$^{-1}$), PDGFβ (10 ng ml$^{-1}$) or media control for 6 h before being collected for mRNA and qPCR analyses. Human PSCs were cultured in IMDM medium containing 20% FBS. Isolated PSCs were ready for use after the second passage. Conditioned medium (CM) from the PSC was collected after 2 days of culture and when cells reached 70-80% confluence. The CM was centrifuged to remove cellular debris before use. BMDMs were prepared as previously described (Xue, J. & Habtezion, A. Carbon monoxide-based therapy ameliorates acute pancreatitis via TLR4 inhibition. *J. Clin. Invest.* 124, 437-447 (2014)). For human monocyte-derived macrophage preparation, human peripheral blood mononuclear cells were isolated from buffy coat using Ficoll-Hypaque density gradient centrifugation, and then monocytes were further enriched by CD14$^+$ magnetic beads (Miltenyi Biotec). Enriched monocytes were cultured with complete RPMI medium containing 50 ng ml$^{-1}$ human macrophage CSF. On day 6, human macrophages are ready for use (Vijayan, D. Isolation and differentiation of monocytes-macrophages from human blood. *Methods Mol. Biol.* 844, 183-187 (2012)). PSC and BMDM coculture experiments were performed in the Transwell system (Corning) in the DMEM/F12 medium with 10% FBS. After seeding $5\times10^4$ PSCs in the bottom well, $5\times10^5$ BMDMs were seeded on the upper mesh (pore size: 0.4 µm). Macrophages were collected for analysis after 48 h of the coculture.

Quantitative RT-PCR: Th pancreas or cells were lysed with Trizol reagent (Invitrogen) for total RNA preparation according to the manufacturer's instructions. Briefly, cDNA was generated using the GoScript reverse transcription system (Promega). Quantitative PCR was performed with an ABI-7900 Sequence Detection System (Applied Biosystems) using designed specific TaqMan probes and primers as follows: YM1 (Forward, 5'-TGGTGAAGGAAATGCG-TAAA-3 (SEQ ID NO: 11); reverse, 5'-GTCAATGATTC-CTGCTCCTG-3 (SEQ ID NO: 12); probe, 5'-AGCAGC-CTTGGAATGTCTTTCTCCA-3'(SEQ ID NO: 13); FIZZ1 forward, 5'-AGGAACTTCCTGCCAATCCA-3'(SEQ ID NO: 14); reverse, 5'-ACAAGCACACCCAGTAGCAG-3' (SEQ ID NO: 15); probe, 5'-CCTCCTGCCCT-GCTGGGATG-3'(SEQ ID NO: 16); ☐ rgl forward, 5'-AGACCACAGTCTGGCAGTTG-3'(SEQ ID NO: 17); reverse, 5'-CCACCCAAATGACACATAGG-3'(SEQ ID NO: 18); probe, 5'-AAGCATCTCTGGCCACGCCA-3' (SEQ ID NO: 19); CD206 (forward, 5'-TGATTACGAGCA-GTGGAAGC-3'(SEQ ID NO: 20); reverse, 5'-GTTCAC-CGTAAGCCCAATTT-3'(SEQ ID NO: 21); probe, 5'-CACCTGGAGTGATGGTTCTCCCG-3'(SEQ ID NO: 22); CD301 forward, 5'-ACTGAGTTCCTGCCTCTGGT-3' (SEQ ID NO: 23); reverse, 5'-ATCTGGGACCAAGGA-GAGTG-3'(SEQ ID NO: 24); probe, 5'-CACTGCTG-CACAGGGAAGCCA-3') (SEQ ID NO: 25); IL-10 forward, 5'-CCCAGAAATCAAGGAGCATT-3'(SEQ ID NO: 26); reverse, 5'-TCA CTCTTCACCTGCTCCAC-3' (SEQ ID NO: 27); probe, 5'-TCGATGACAGCGCCTCA-GCC-3'(SEQ ID NO: 28); TGFβ forward, 5'-CCCTAT-ATTTGGAGCCTGGA-3'(SEQ ID NO: 29); reverse, 5'-CTTGCGACCCACGTAGTAGA-3'(SEQ ID NO: 30); probe, 5'-CCGCAGGCTTTGGAGCCACT-3'(SEQ ID NO: 31); inducible nitric oxide synthase forward, 5'-ACCTTGT-TCAGCTACGCCTT-3'(SEQ ID NO: 32); reverse, 5'-TCT-TCAGAGTCTGCCCATTG-3'(SEQ ID NO: 33); probe, 5'-TGCTCCTCTTCCAAGGTGCTTGC-3'(SEQ ID NO: 34); TNFα forward, 5'-CCAAAGGGATGAGAAGTTCC-3'(SEQ ID NO: 35); reverse, 5'-CTCCACTTGGTGGTTT-GCTA-3'(SEQ ID NO: 36); probe, 5'-TGGCCCAGACCCT-CACACTCA-3 '(SEQ ID NO: 37); αSMA forward, 5'-CTCCCTGGAGAAGAGCTACG-3'(SEQ ID NO: 38); reverse, 5'-TGA CTCCATCCCAATGAAAG-3'(SEQ ID NO: 39); probe, 5'-AAACGAACGCTTCCGCTGCC-3) (SEQ ID NO: 40); CollegenlAl (forward, 5'-AGAAGGC-CAGTCTGGAGAAA-3'(SEQ ID NO: 41); reverse, 5'-GAG CCCTTGAGACCTCTGAC-3'(SEQ ID NO: 42); probe, 5'-TGCCCTGGGTCCTCCTGGTC-3'(SEQ ID NO: 43); Fibronectin forward, 5'-TGGTGGCCACTAAATACGAA-3' (SEQ ID NO: 44); reverse, 5'-GGAGGGCTAACATTCTC-CAG-3'(SEQ ID NO: 45); probe, 5'-CAAGCAGACCAGC-CCAGGGA-3 '(SEQ ID NO: 46); TIMP1 forward, 5'-CCAGAAATCAACGAGACCAC-3'(SEQ ID NO: 47); reverse, 5'-GGCATATCCACAGAGGCTTT-3'(SEQ ID NO: 48); probe, 5'-TCTGCGGCATTTCCCACAGC-3'(SEQ ID NO: 49); MMP9 (forward, 5'-TCCTTGCAATGTGGAT-GTTT-3'(SEQ ID NO: 50); reverse, 5'-CTTCCAGTAC-CAACCGTCCT-3'(SEQ ID NO: 51); probe, 5'-TGCA-GAGCGCCTGGATCTC-3'(SEQ ID NO: 52); GAPDH (forward, 5'-TGTGTCCGTCGTGGATCTGA-3'(SEQ ID NO: 53); reverse, 5'-CCTGCTTCACCACCTTCCTTGA-3' (SEQ ID NO: 54); probe, 5'-CCGCCTGGAGAAACCTGC-CAAGTATG-3'(SEQ ID NO: 55). Samples were normalized to GAPDH and displayed as fold induction over untreated controls, unless otherwise stated.

Statistical analysis: Unpaired Student's t-test was used to determine statistical significance, unless otherwise indicated, and P value of less than 0.05 was considered significant. Where indicated, one-way analysis of variance and Tukey's post hoc test was used as described in figure legend. Values are expressed as mean±s.e.m. (Prism 5; GraphPad Software). Unless indicated, results are from at least three independent experiments.

Example 3

Macrophages are Increased in Mouse and Human CP.

Studies on pathogenic mechanism of fibrosis in human CP are restricted by limited availability of tissues obtained from surgery. Therefore, animal models, despite their limitation in recapitulating all aspects of human disease, have been useful to investigate the initiation and progression of CP (Saluja, A. K. & Dudeja, V. *Gastroenterology* 144, 1194-1198 (2013); Lerch, M. M. & Gorelick, F. S. *Gastroenterology* 144, 1180-1193 (2013)). In mice, hyperstimulation of the pancreas with cholecystokinin analogue caerulein leads to AP, and continuous acute injury to the pancreas drives chronic inflammation of the pancreas (Witt, H., et al. *Gastroenterology* 132, 1557-1573 (2007); Lerch, M. et al. *Gastroenterology* 144, 1180-1193 (2013)). To generate experimental CP, we induced AP in a repetitive manner over 4 weeks (three times per week). Mice undergoing repetitive treatment with caerulein revealed morphologic signs of CP with leukocyte infiltration, pancreatic fibrosis and acinar cell loss corresponding to small size of the pancreas relative to body weight.

We next sought to investigate the immune responses in experimental CP. Using Luminex assay, we compared multiple cytokine and chemokine expression profiles in the pancreas from control and CP mice. As expected, the pro-fibrotic cytokine, transforming growth factor beta (TGFβ was increased in the pancreas of CP mice. However, pro-inflammatory cytokines (IL-1β and IL-6), which are known to be increased during acute inflammation, were downregulated in CP. Chronic repeated caerulein administration and pancreas harvest 3 days after the last injection is consistent with the development of a chronic and not AP. Furthermore, macrophage-associated cytokines and chemokines (granulocyte-macrophage CSF, granulocyte CSF, chemokine (C—C motif) ligand (CCL)2/monocyte-specific chemokine (MCP)-1, CCL7/MCP-3 and CCL3/macrophage inflammatory protein (MIP)1A) were upregulated, suggesting that monocytes/macrophages play an important role during CP. In contrast, no significant increase in CXCL1, a neutrophil chemoattractant with role in AP (Zhang, H. et al. *J. Clin. Invest.* 123, 1019-1031 (2013)), was observed (FIG. 2A).

Figure 2C:
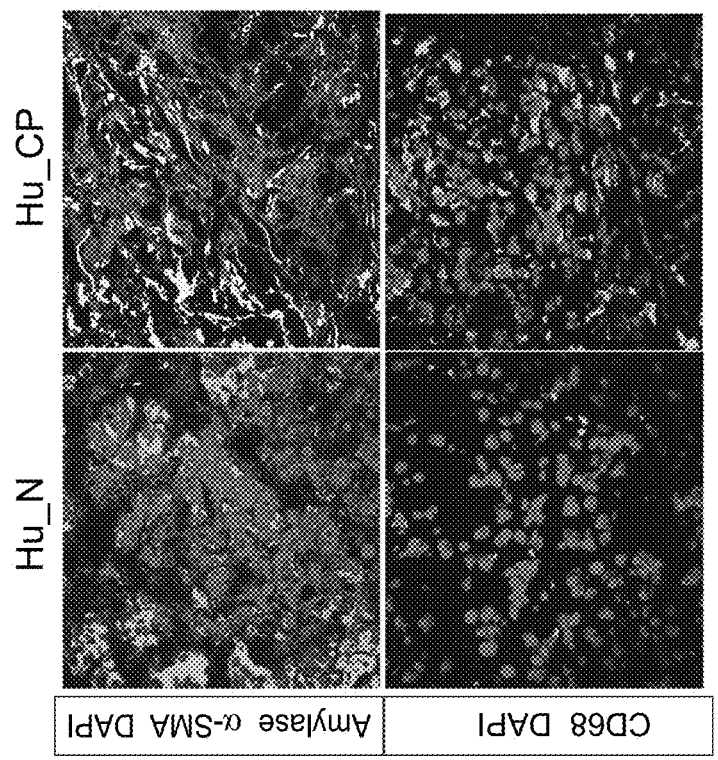
Figure 2B:
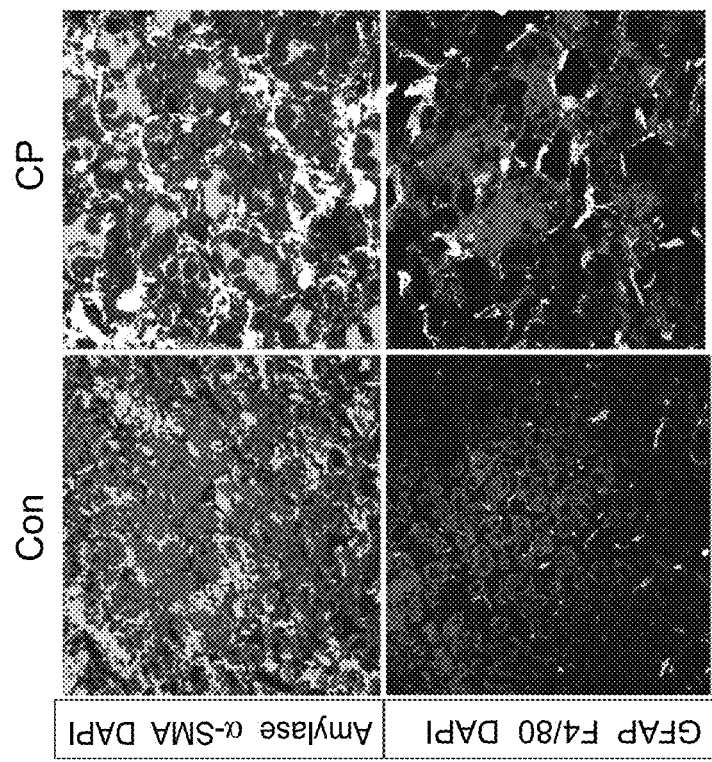

To understand the relevance of these observations to human CP, we compared them with normal pancreas tissue sections. Immunofluorescence analysis showed that CD68$^+$ macrophages were increased in human CP (FIG. 2C). A similar trend was observed in mice; macrophage marker F4/80 analysis revealed that macrophages are abundant in CP as compared with the normal pancreas of mice (FIG. 2B). Furthermore, the number of pancreatic macrophages (CD11b$^+$F4/80$^+$) analysed using flow cytometry was markedly increased in CP mice (FIG. 2D). Macrophage tissue infiltration occurs in two distinct ways: recruitment of monocyte precursors and proliferation of resident cells (Jenkins, S. J. et al. *J. Exp. Med.* 210, 2477-2491 (2013)). We used Ki-67 expression and 5-bromodeoxyuridine (BrdU) incorporation to determine the proportion of proliferating macrophages. We found that BrdU$^+$ and Ki-67$^+$ macrophages were both increased in CP mice accounting for ~12-25% of the pancreatic macrophages (FIG. 2D), indicating proliferation of either resident macrophages or recruited monocytes that differentiated to macrophage contributed to some of the macrophage accumulation in CP.

During AP, monocytes are attracted to the injured pancreas before their differentiation into macrophages in a CCR2-dependent manner (Saeki, K. et al. *Gastroenterology* 142, 1010-1020 e1019 (2012); Serbina, N. V. & Pamer, E. G. *Nat. Immunol.* 7, 311-317 (2006)). CCR2 ligands such as CCL2 (MCP-1) and CCL7 (MCP-3) are also elevated in CP (FIG. 2A). Considering that the model of CP is based on repetitive acute injury, we hypothesized that, in addition to proliferation, a significant proportion of macrophages in CP arises from monocyte recruitment. A competitive bone marrow (BM) chimera was set up by lethally irradiating recipient $CCR2^{WT}CD45.1^+$ $CD45.2^+$ C57BL/6 mice and reconstituting them with a 1:1 mixture of BM derived from CCR2 wild-type (WT; $CCR2^{WT}$ $CD45.1^+$) and CCR2 knockout ($CCR2^{KO}$ $CD45.2^+$) mice so that macrophages derived from $CCR2^{KO}$ and $CCR2^{WT}$ mice could be distinguished from one another as well as from those of the recipient mice based on the allotypic CD45 markers. Following 8 weeks of engraftment and induction of CP, we found that the number of $CCR2^{WT}$ macrophages greatly outnumbered $CCR2^{KO}$ macrophages. However, there was no difference in proliferation (BrdU incorporation) observed between $CCR2^{WT}$ and $CCR2^{KO}$ cells, supporting CCR2's role in monocyte recruitment as a significant contributor to macrophage accumulation in CP (FIG. 2E).

CP was induced in non-irradiated wild-type ($CCR2^{WT}$) and CCR2 knockout ($CCR2^{KO}$ mice). CCR2 deficiency limits pancreatic macrophage accumulation in CP, and no proliferation difference is observed between presence and absence of CCR2, which is consistent with the above BM chimera findings. However, in the absence of CCR2 there is still monocyte/macrophage recruitment to the pancreas during CP, suggesting that CCR2-independent mechanism(s) also exist. Thus, both monocyte recruitment (via CCR2-dependent and -independent mechanisms) and macrophage proliferation account for macrophage accumulation during CP progression.

Example 4

AAMs are Dominant in Mouse and Human CP

Figure 3A:
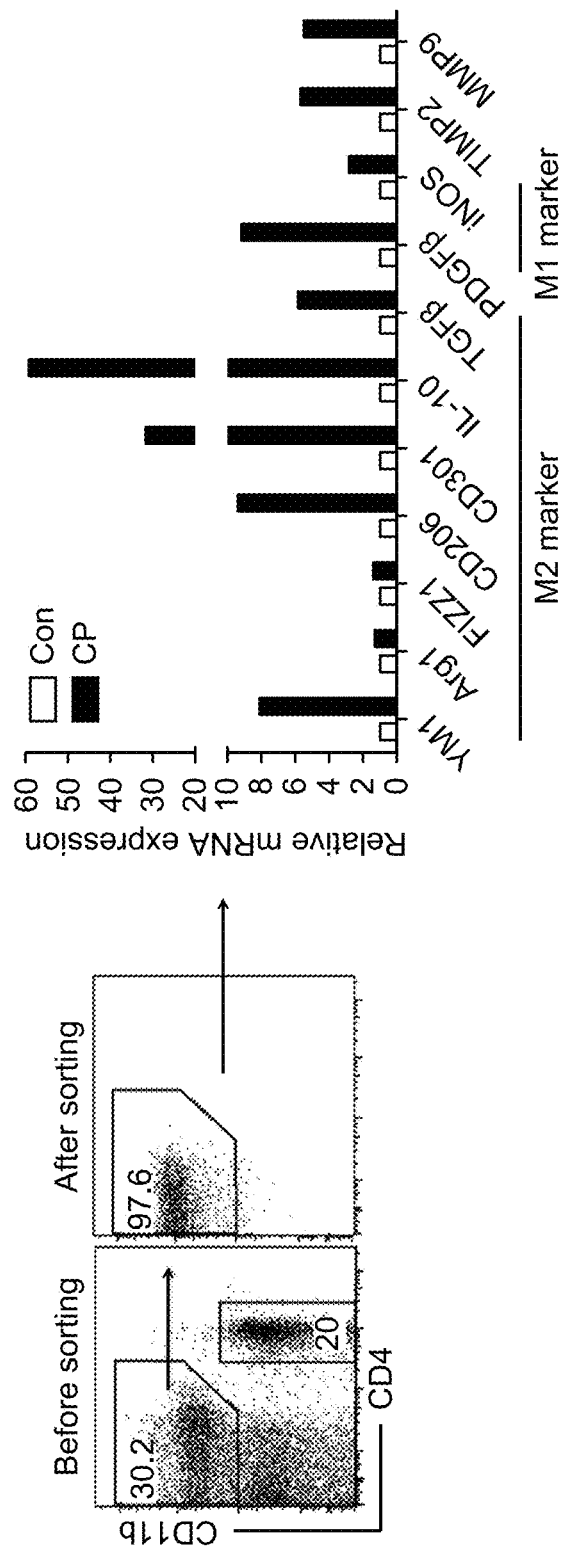
Figure 3B:
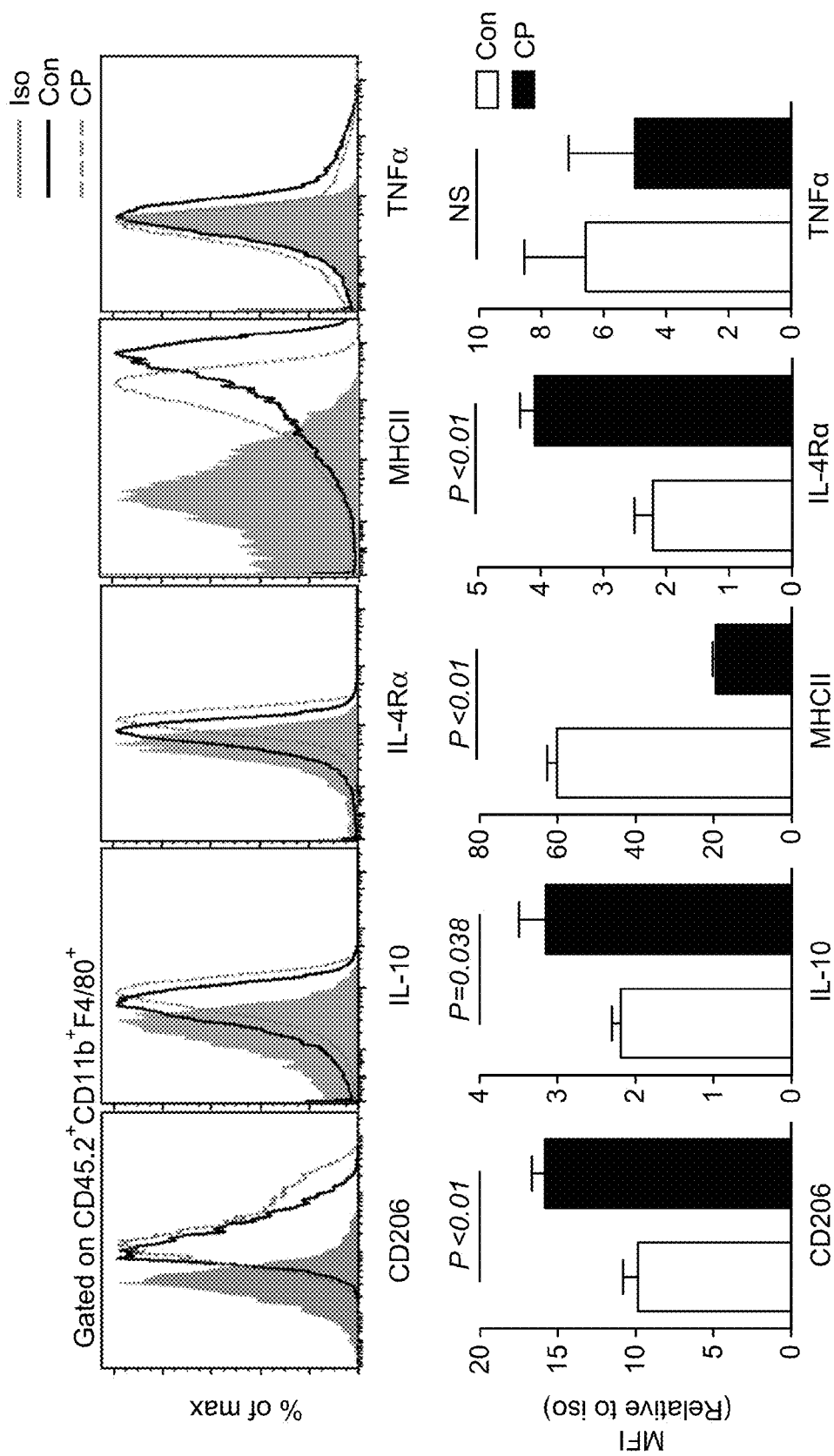

In order to determine the polarization state of macrophages in CP, $SSC-A^{low}CD11b^+$ monocytes/macrophages were sorted from both control and CP mice for gene expression analysis. Gene expression profile revealed an increase in M2-associated genes, such as YM1, CD206, CD301, IL-10, TGFβ, and PDGFβ, in pancreatic monocytes/macrophages of CP as compared with controls (FIG. 3A). Moreover, the presence of AAMs in CP was further verified using flow cytometry as shown by increased M2-associated markers (CD206, IL-10 and IL-4Rα), and decreased or unchanged expression of M1-associated markers (major histocompatibility complex class II (MHCII) and tumor-necrosis factor alpha (TNFα) (FIG. 3B). In contrast, by assessing dynamic gene expression of pancreatic macrophages during AP induction, classical activation profile with increased TNFα and decreased CD206, CD301 was found in AP mice. Unlike TNFα, IL-10 expression can be seen as late response in M1s (Murray, P. J. & Wynn, T. A. *J. Leukoc. Biol* 89, 557-563 (2011)). Nevertheless, IL-10 in AP is expressed at much lower level as compared with CP in pancreatic macrophages (FIG. 3A-FIG. 3B), although not to the same extent, slightly higher level of YM1 expression is seen in CP as compared with AP. Arg1 has recently been shown to be expressed by both classic and AAMs (Murray, P. J. et al. *Immunity* 41, 14-20 (2014)). Flow cytometric data were consistent with the histologic analysis of pancreas from CP mice on the basis of immunofluorescence staining where a majority of $F4/80^+$ macrophages were positive for CD206 but not TNFα. Similar findings were observed in human CP tissues, where $CD68^+$ cells expressed CD206, but not TNFα (FIG. 3C, FIG. 3D).

Example 5

PSCs Promote Alternative Activation of Macrophages.

Macrophages are highly heterogeneous cells that can rapidly change their activation status and function in response to local micro-environment signals (Sica, A. & Mantovani, A. *J. Clin. Invest.* 122, 787-795 (2012); Murray, P. J. & Wynn, T. A. *Nat. Rev. Immunol.* 11, 723-737 (2011)). In light of the crucial role played by PSCs in CP, we asked whether PSCs might contribute to macrophage polarization and function. We isolated PSCs from CP mice and assessed their cytokine production with the Luminex assay. Overall, the expression of several pro-inflammatory cytokines such as IFNγ, TNFα and IL-1β was very low. In contrast, PSCs secreted higher levels of IL-4, IL-5, IL-13, IL-10 and TGFβ, indicating a Th2 and profibrogenic cytokine bias (FIG. 4A).

To explore whether factors released by PSCs have the ability to change the activation and polarization status of pancreatic macrophages, we cocultured BM-derived macrophages (BMDMs) with the PSCs in vitro. BMDMs after being cocultured with activated PSCs exhibited alternative activation (M2) profile with increased CD206, CD301, IL-10, TGFβ and PDGFβ mRNA expression but had decreased expression of inducible nitric oxide synthase (M1 marker; FIG. 4B). Moreover, conditioned medium from the PSCs resulted in upregulation of CD206, IL-10 and IL-4Rα, and downregulation of MHCII and TNFα expression (FIG. 4C), suggesting that factors released by PSCs promoted macrophage polarization towards M2.

Figure 4E:
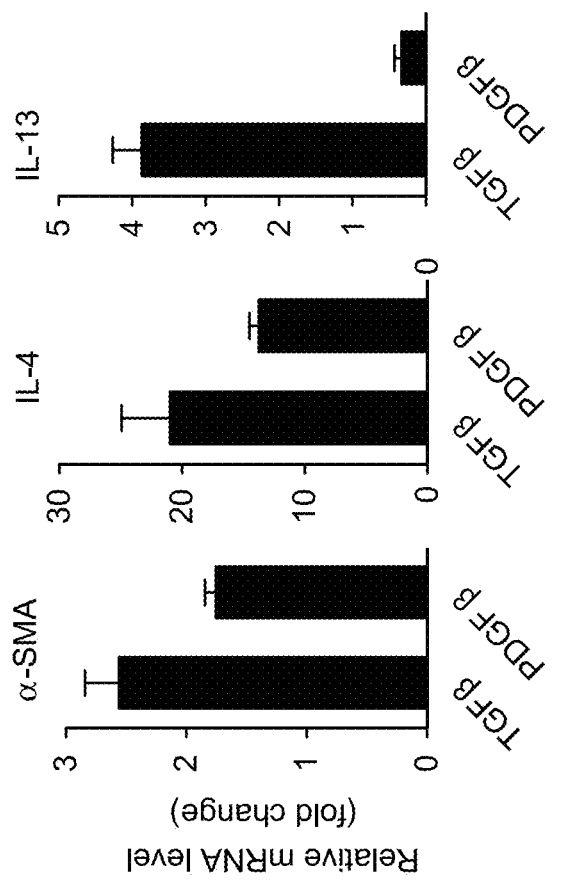
Figure 4D:
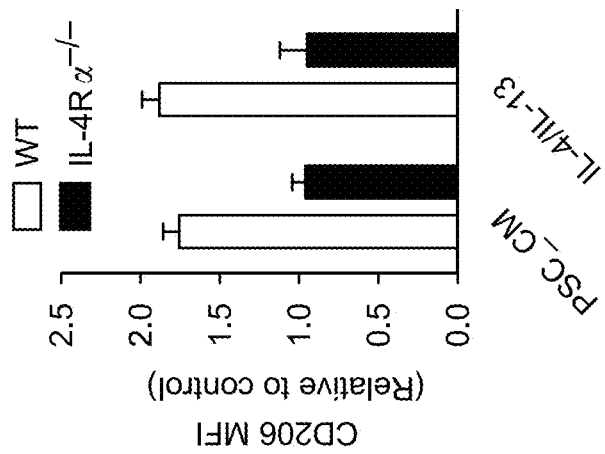

Th2 cytokines such as IL-4/IL-13 mediate alternate activation of macrophages via IL-4 receptor. Thus, we tested whether the PSC supernatant is mediating M2 polarization via IL-4Rα using BMDMs from WT and IL-4Rα$^{-/-}$ mice. Compared with WT BMDMs, IL-4Rα$^{-/-}$ BMDMs were unable to be alternatively activated by the conditioned medium from the PSCs (FIG. 4D). Moreover, PSC conditioned medium was as good as exogenously added IL-4/IL-13, standard M2 polarizing conditions. The macrophages produced TGFβ and PDGFβ (FIG. 4B), previously shown to be potent activators of PSCs (Omary, M. B., et al. *J. Clin. Invest.* 117, 50-59 (2007)). To investigate the effect of these factors on PSC-mediated macrophage polarization, we treated PSCs with TGFβ and PDGFβ and examined the expression of IL-4/IL-13. Our study shows that PDGFβ and in particular TGFβ were capable not only of inducing alpha smooth muscle actin (α-SMA) but also IL-4 and IL-13 genes in the PSCs (FIG. 4E). Taken together, these results suggest that PSCs promote macrophage alternative activation in an IL-4Rα signaling-dependent manner, and the macrophages in turn have the ability to induce PSC activation and produce IL-4R ligands.

To further validate our finding in human, we isolated PSCs from six patients (hPSCs) who underwent surgical resection (three from normal pancreas, three from pancreatic cancer) of the pancreas. We confirmed that the cultured cells had a PSC phenotype using immunofluorescence staining of Glial fibrillary acidic protein (GFAP) and α-SMA. Consistent with mouse PSCs, hPSCs secreted relatively higher levels of Th2 as compared with Th1 cytokines (FIG. 4F). Macrophages derived from circulating monocytes of healthy blood donors were cocultured with supernatant of the hPSCs in an effort to translate the mouse studies. Conditioned medium from all six hPSCs increased CD206, but decreased TNFα expression in the human macrophages, indicating that factors released from hPSCs also promote macrophage polarization towards M2 (FIG. 4G).

Example 6

IL-4Rα Signal Deficiency Limits AAMs and Protects Against CP

Figure 5B:
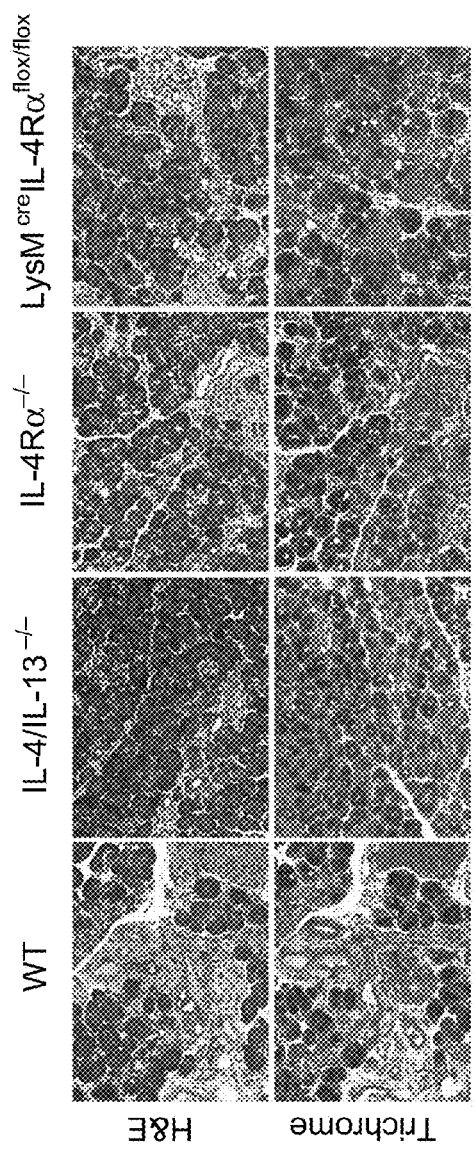
Figure 5A:
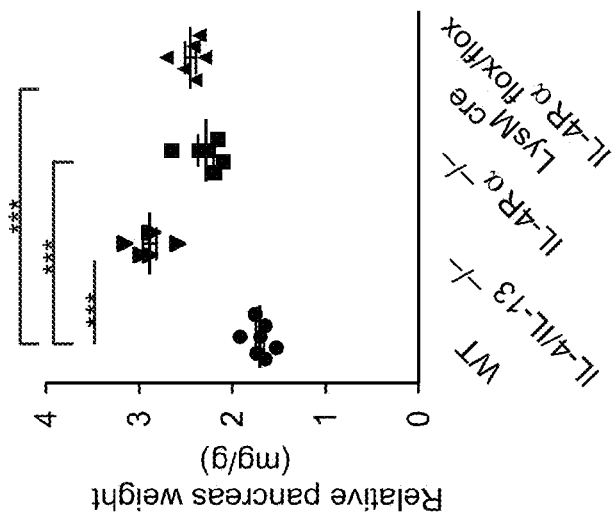
Figure 5D:
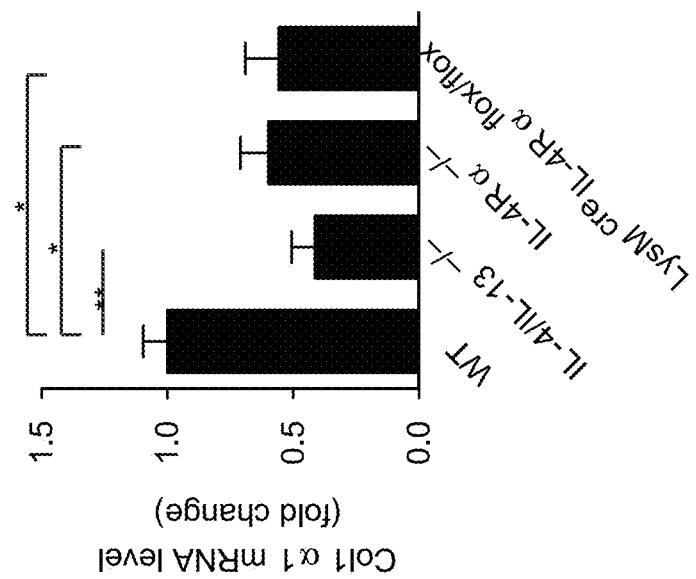
Figure 5C:
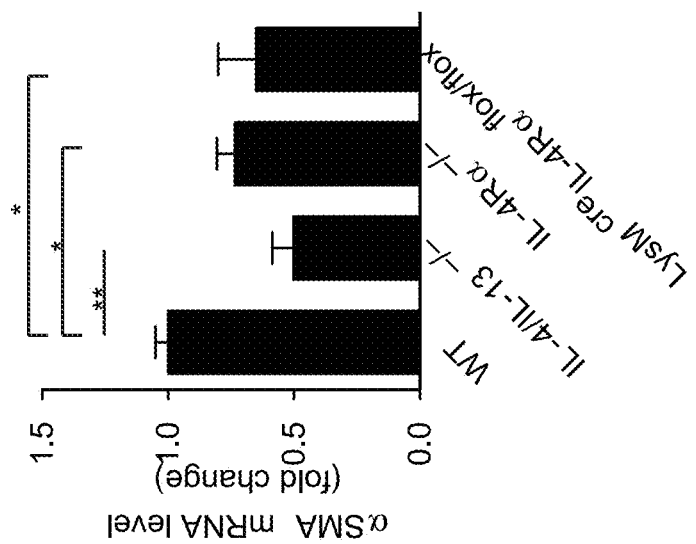
Figure 5E:
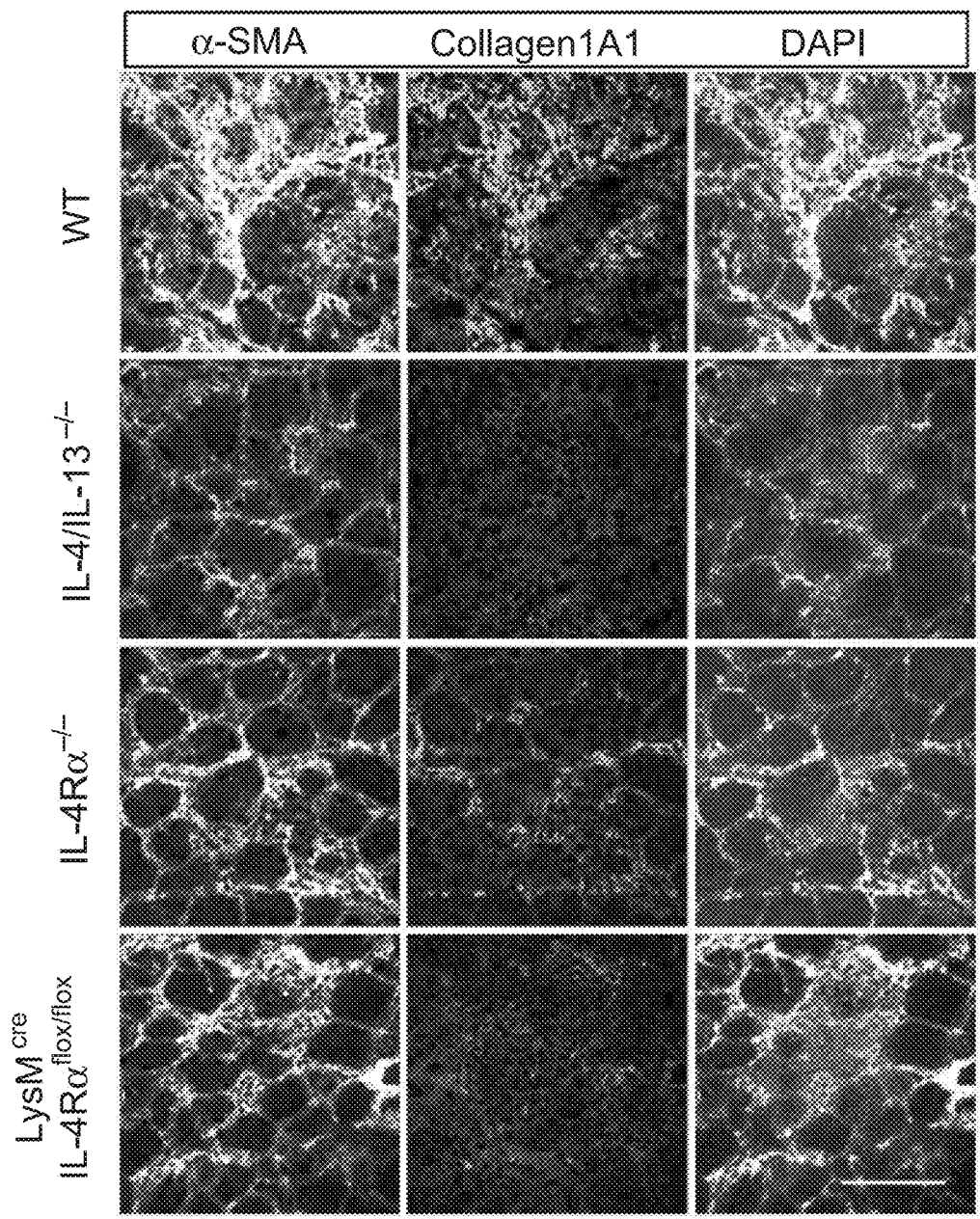

To investigate the importance of macrophage alternative activation in CP, we induced CP in mice lacking IL-4 and IL-13. IL-4/IL-13$^{-/-}$ mice have been shown to lack AAMs in other disease models (Nguyen, K. D. et al. *Nature* 480, 104-108 (2011)). Unlike WT counterparts, IL-4/IL-13$^{-/-}$ mice were less susceptible to CP, as shown by the larger relative pancreas size (WT: from 5.95±0.11 to 1.71±0.05IL-4/IL/13$^{-/-}$; from 5.98±0.20 to 2.89±0.07; FIG. 5A), lower fibrosis-associated gene expression in the pancreas such as α SMA (α-SMA) and Col1α1 (Collagen1A1) using real-time PCR and immuno-fluorescence analysis (FIG. 5B, FIG. 5C). Moreover, compared with WT mice, macrophages isolated from the IL-4/IL-13$^{-/-}$ mice pancreas had lower expression of CD206, suggesting a decrease in alternative activation of pancreatic macrophages (FIG. 5D).

To determine whether the observed decrease in pancreatic fibrosis was a direct consequence of IL-4Rα signaling, we used mice with global deletion of IL-4Rα and LysM$^{cre}$IL-4Rα$^{flox/flox}$ mice, where IL-4Rα is deleted specifically in myeloid cells (i.e., macrophages and neutrophils) to induce CP (Nguyen, K. D. et al. *Nature* 480, 104-108 (2011); Herbert, D. R. et al. *Immunity* 20, 623-635 (2004)). As expected, pancreatic macrophages from IL-4Rα$^{-/-}$ and LysM$^{cre}$IL-4Rα$^{flox/flox}$ mice displayed impaired alternative activation under chronic inflammation (FIG. 5F). IL-4Rα$^{-/-}$ and LysM$^{cre}$IL-4Rα$^{flox/flox}$ mouse pancreas were less fibrotic and had lower expression of fibrosis-associated markers (α-SMA and Collengen1A1) as compared with their WT counterparts (FIG. 5A-FIG. 5E). Notably, IL-4Rα$^{-/-}$ and LysM$^{cre}$IL-4Rα$^{flox/flox}$ mice showed no obvious difference in pancreatic fibrosis and alternative macrophage activation, suggesting that the protective effect of IL-4Rα inhibition is mediated via absence of this receptor or signaling on myeloid cells or macrophages. Thus, in this model of CP, AAMs are important contributors to disease pathogenesis.

To further confirm an IL-4Rα requirement for macrophage alternative activation in CP, we set up a mixed BM chimera with a 1:1 BM reconstitution from IL-4Rα$^{WT}$ CD45.1$^{+}$ and IL-4Rα$^{-/-}$ CD45.2$^{+}$ mice in order to compare IL-4Rα-sufficient and -deficient macrophages in the same environment of CP. In such a competitive environment, CD206 expression in IL-4Rα$^{WT}$ macrophages (CD11b$^{+}$F4/80$^{+}$) was upregulated following CP induction, whereas no significant difference in CD206 expression was observed in IL-4Rα$^{-/-}$ macrophages. No difference in proliferation between IL-4Rα$^{WT}$ and IL-4Rα$^{-/-}$ pancreatic macrophages was observed. In sum, these findings indicate that IL-4Rα signalling in macrophages is in part required for pancreatic macrophage alternative activation and fibrosis during CP development.

Example 7

IL-4/IL-13 Blockade Ameliorates Established CP.

Figure 6A:
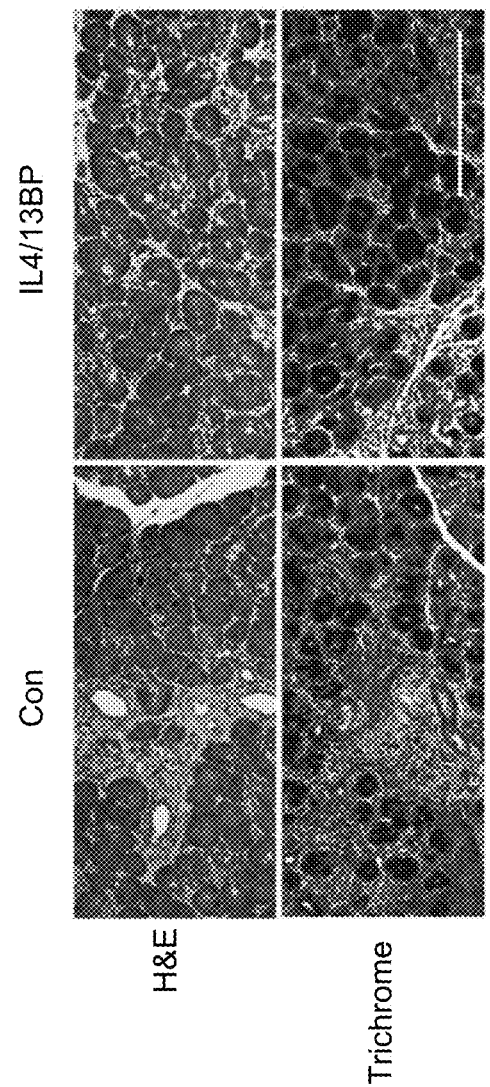
Figure 6B:
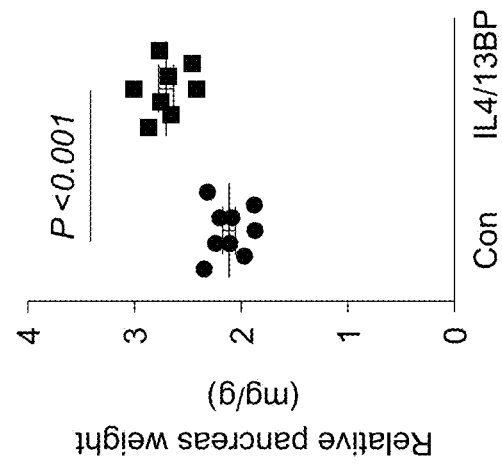
Figure 6D:
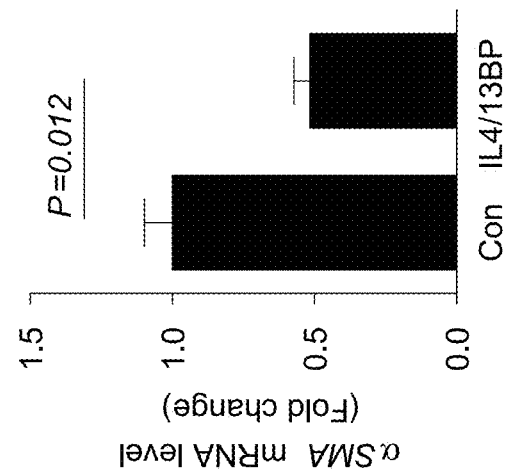
Figure 6C:
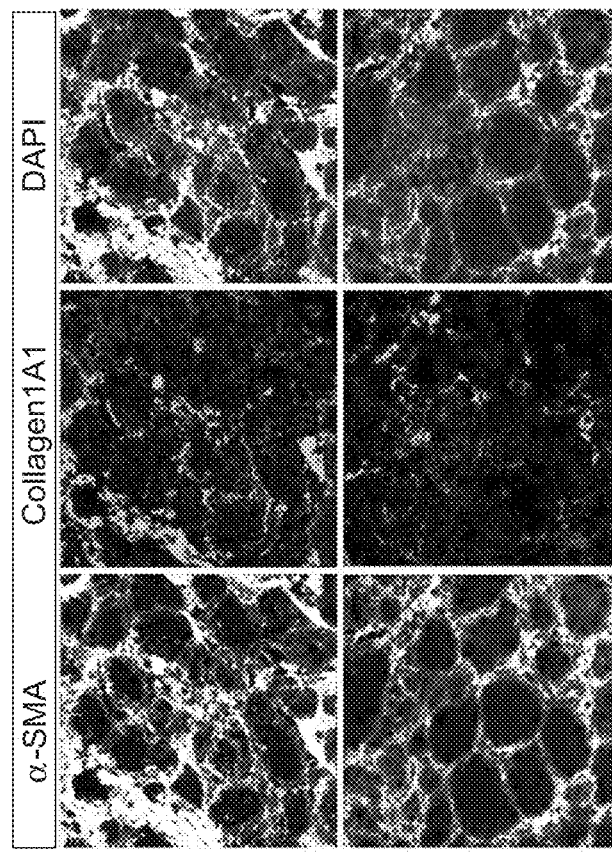

In light of the above findings and the importance of IL-4Rα signaling in experimental CP-associated fibrogenesis, we wanted to test whether IL-4Rα signaling blockade can be used as a therapy in established disease. We used IL-4/IL-13-blocking peptide (CSRM53567). We first tested the inhibitor in an in vitro titration assay, and at 1 μM the inhibitor significantly decreased mouse IL-4/IL-13-induced M2 polarization and CD206 expression. We then tested the effect of the inhibitor in mice that were already subjected to repeated caerulein injection for 2 weeks, where significant decrease in pancreas size and α-SMA expression was present. Compared with control treatment group, the inhibitor treatment limited pancreas fibrosis (FIG. 6A-FIG. 6E). Furthermore, blockade of alternative activation of pancreatic macrophages by the inhibitor was confirmed using flow cytometry (FIG. 6F). These observations, as a proof-of-concept, demonstrate potential for treating CP. We then tested the inhibitor's ability in blocking M2 polarization of human macrophage by the hPSCs. The peptide was indeed capable of inhibiting hPSC-mediated M2 polarization of human macrophages (FIG. 6G).

Example 8

Generally, CP is accepted as an irreversible and fibrotic disease, and current management is supportive at best with focus in controlling pain and complications associated with the exocrine and endocrine loss of functions (Witt, H., et al. *Gastroenterology* 132, 1557-1573 (2007)). Following the discovery and the central role of PSCs in pancreatic fibrosis, potential treatment approaches in CP have proposed inhibition or inactivation of PSCs (Talukdar, R. & Tandon, R. K. *J. Gastroenterol. Hepatol.* 23, 34-41 (2008)). However, the immune responses and immune cell contribution to PSC activation during CP progression remain poorly understood. In the current study, we explore the characteristics and role of macrophages, as well as aim to identify mechanisms for macrophage interaction with PSCs in CP. Our results show that AAMs play an important role in CP fibrogenesis and identify the key pathway that can be potentially targeted.

Macrophages have been proposed as the master regulators of inflammation and fibrosis in diseases such as liver fibrosis and systemic sclerosis (Wynn, T. A. & Barron, L. *Semin. Liver Dis.* 30, 245-257 (2010)). Our study reveals that macrophages are increased in both mouse and human CP. CP is also associated with an increase in macrophage-related cytokines and chemokines, supporting for a critical role of macrophages in disease progression. Since macrophages differentiate as well as polarize in tissues and do not recirculate, our data using competitive BM chimeras and proliferation studies suggest that both local (in situ) macrophage proliferation and monocyte recruitment contribute to the macrophage accumulation in CP.

In sharp contrast to AP where M1 predominate, CP favored alternative activation of macrophages. Macrophages represent a spectrum of activated phenotypes rather than a discrete stable subpopulation (Mosser, D., M. & Edwards, J. P. *Nat. Rev. Immunol.* 8, 958-969 (2008)), and it is possible that macrophages in different activation states or mixed phenotypes coexist as have been shown under different physiological and pathological conditions (Kawanishi, N., et al. *Exerc. Immunol. Rev.* 16, 105-118 (2010)). Indeed, these phenomena may account for the varied expression level of some of the M2 markers (for example, YM1). Macrophages in our CP model and those from PSC cocultures had higher mRNA expression of TGFβ and PDGFβ, suggesting possible role in directly promoting proliferation and activation of PSCs (Omary, M. B., et al. *J. Clin. Invest.* 117, 50-59 (2007); Apte, M. V. et al. *Gut* 44, 534-541 (1999); Shek, F. W. et al. *Am. J. Pathol.* 160, 1787-1798 (2002)). These macrophages express higher levels of tissue inhibitor metalloproteinase 2 (TIMP2) and matrix metalloproteinase 9 (MMP9) and thus may also regulate extracellular matrix turnover (FIG. 3A). Moreover, their expression of IL-10 and downregulation of MHCII suggest immunosuppressive properties.

Several studies have documented macrophage plasticity with these cells switching from one functional phenotype to another in response to variable local microenvironmental signals (Kawanishi, N., et al. *Exerc. Immunol. Rev.* 16, 105-118 (2010); Stout, R. D. et al. *J. Immunol.* 175, 342-349 (2005); Stout, R. D. & Suttles, J. *J. Leukoc. Biol.* 76, 509-513 (2004); Porcheray, F. et al. *Clin. Exp. Immunol.* 142, 481-489 (2005)). In light of the central role of PSCs in CP progression, we took into account that the PSCs may be providing signals to maintain and facilitate the increased alternative activation observed in CP. In fact, relative to pro-inflammatory cytokines, PSCs (from both mouse and human pancreas) expressed higher levels of Th2 cytokines, IL-4 and IL-13, which are required for macrophage alternative activation (Gordon, S. *Nat. Rev. Immunol.* 3, 23-35 (2003); Van Dyken, S. J. & Locksley, R. M. *Annu. Rev. Immunol.* 31, 317-343 (2013)). Furthermore, using IL-4Rα-sufficient and -deficient mixed BM chimeras, we confirmed that IL-4Rα signaling is required for alternative activation of macrophages in CP.

Both IL-4Rα$^{-/-}$ and LysM$^{cre}$IL-4Rα$^{flox/flox}$ mice had similar decreases in pancreatic fibrosis and PSC activation (α-SMA), suggesting that the contribution of IL-4Rα signaling in fibrosis during CP is myeloid- or macrophage-dependent. IL-4/IL-13$^{-/-}$ mice were even less susceptible to caerulein-induced CP. Similar to IL-4, IL-13 signals through the IL-4 receptor (a heterodimeric receptor composed of IL-4Rα and IL-13Rα1); however, IL-13 can also bind to IL-13Rα2 (which does not bind IL-4) to trigger downstream signals. IL-13 has been shown to be a major inducer of fibrosis in many chronic infectious and autoimmune diseases in part via the IL-13Rα2 (ref. 34). Inhibition of both IL-4 receptor and IL-13Rα2 signaling in the double knockout mice (IL-4/IL-13$^{-/-}$) as compared with inhibition of the IL-4 receptor only in the IL-4Rα$^{-/-}$ and LysM$^{cre}$IL-4Rα$^{flox/flox}$ mice may account for the increased protection against CP development observed in the IL-4/IL-13$^{-/-}$ mice.

Functional macrophage polarization is observed in vivo under physiological and pathological conditions (Sica, A. & Mantovani, A. *J. Clin. Invest.* 122, 787-795 (2012)). The phenotype of polarized M1 or M2 macrophages can, to some extent, be reversed in vitro and in vivo (Saccani, A. et al. *Cancer Res.* 66, 11432-11440 (2006); Guiducci, C., et al. *Cancer Res.* 65, 3437-3446 (2005)). Therefore, reorienting and reshaping macrophage polarization has been considered as a therapeutic strategy for several diseases. In our study, we attempted to reshape macrophage polarization through genetically deficient mice or via blocking IL-4/IL-13 by pharmacological means. Consistent with results from IL-4/IL-13-deficient mice, treatment with the IL-4/13-blocking peptide following induction of CP decreased macrophage alternative activation and ameliorated pancreatic fibrosis. This immune-based therapy in experimental CP challenges the thinking that CP cannot be actively treated, reversed or halted from progressing. Future studies determining the contribution of IL-4 versus IL-13 will be of interest to further define and design specific target(s).

Figure 7:
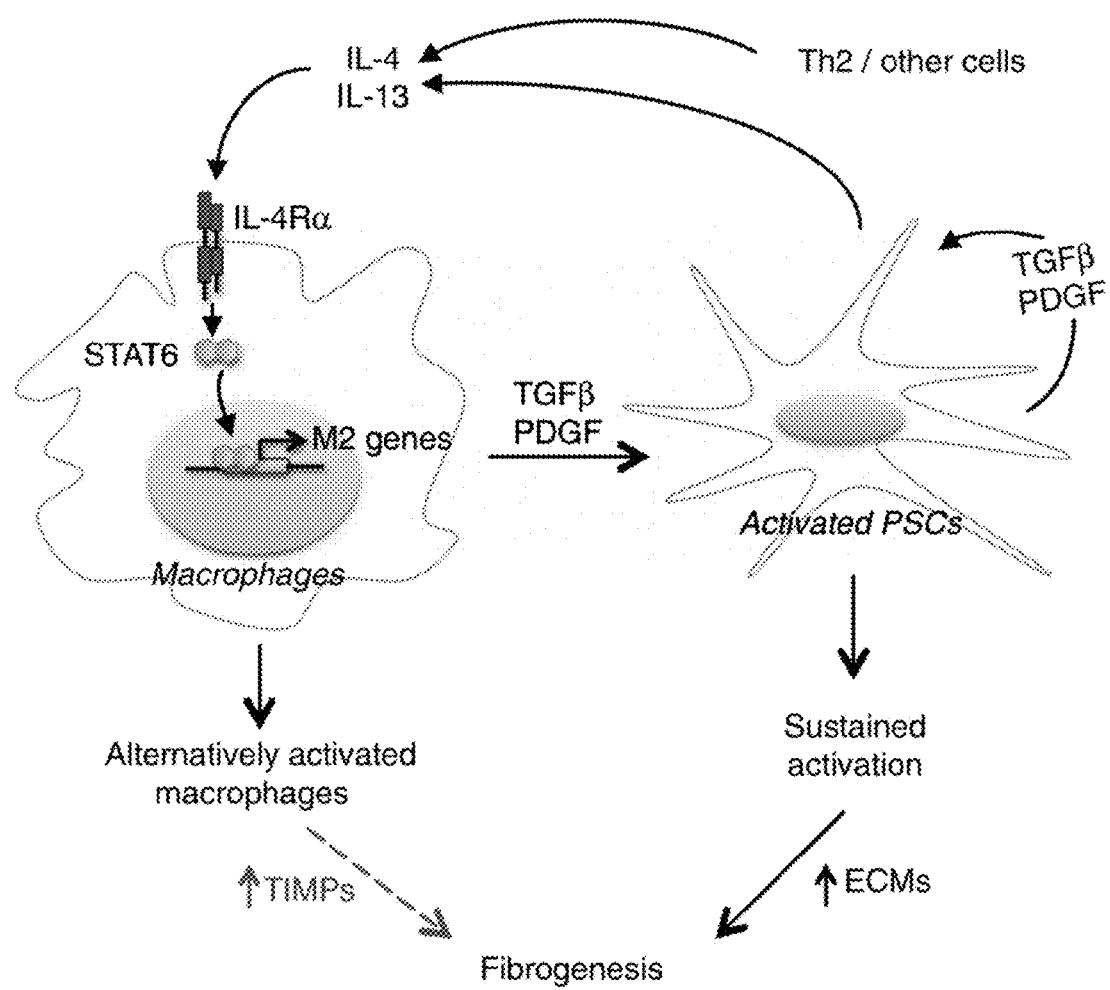
FIG. 7 depicts, in accordance with various embodiments of the present invention, a schematic representation of macrophage and pancreatic stellate cell (PSC) interation in chronic pancreatitis.

Our in vitro human PSCs and macrophage coculture experiments are consistent with the results obtained in mouse studies. We show that activated mouse and human PSCs secrete Th2 cytokines and enhance M2 polarization, leading to a potentially perpetual feed forward process (FIG. 7). These findings are confirmed using IL-4Rα-deficient macrophages, and IL-4/IL-13-blocking peptide in experimental mouse and human systems. Interfering with IL-4Rα signaling and/or PSC activation is likely to turn off this feed forward process in CP. Our in vitro human studies, together with results observed from mouse studies, provide a proof-of-concept for potential targetable pathway and first step towards bench to bedside translation.

Example 9

Figure 8A:
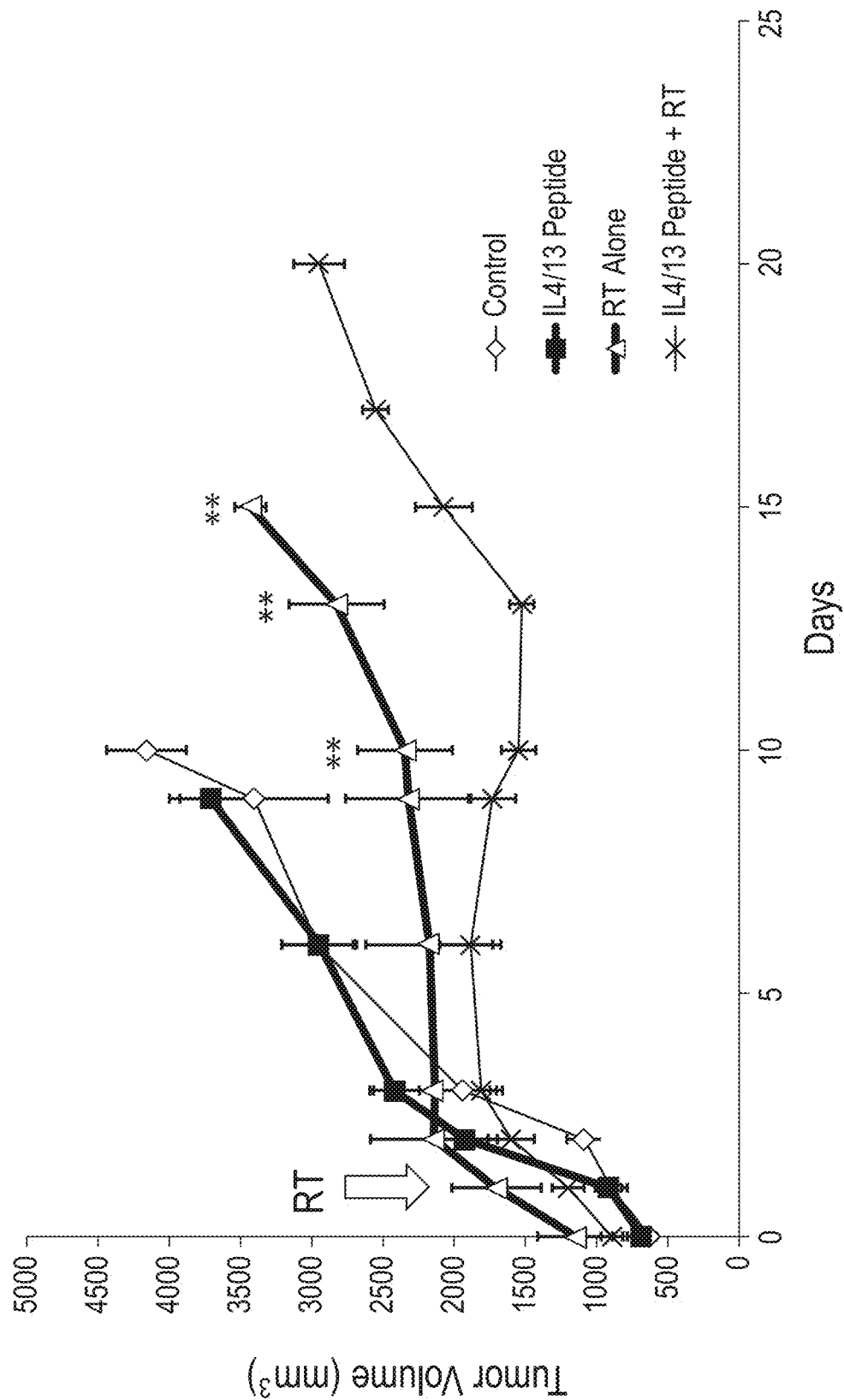
FIG. 8A-FIG. 8B depict, in accordance with various embodiments of the present invention.

Syngeneic E0771 tumors were implanted in the lower mammary gland of C57BL/6 mice and allowed to grow to approximately 1000 mm$^3$. Mice were then enrolled on study (n=5/group) and treated with either PBS (Control), IL4/13 blocking peptide CSRM53567 (50 μg in 100 μL PBS, daily injection), radiation therapy (RT) alone (16 Gy) or combination of CSRM53567 peptide and RT. Mice were measured at the indicated time points with digital calipers and the resulting volume was calculated. **$p<0.01$. As shown in FIG. 8A, the IL4/13 blocking peptide enhances response to radiation therapy.

Figure 8B:
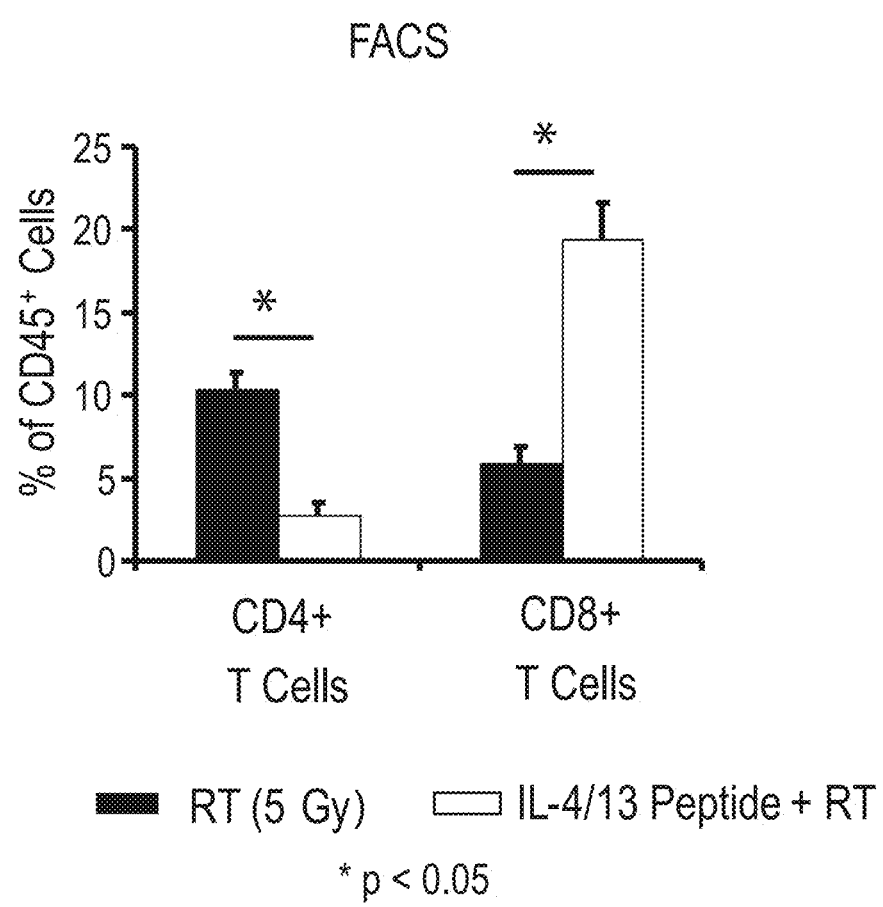

There were fewer CD4+ T cells and more CD8+ T cells as a percentage of the CD45+ leukocytes in the tumors that received radiation therapy and the IL4/13 blocking peptide compared to radiation alone. However, the absolute number of CD45+ leukocytes remained roughly the same. The cytokines and CD45+ cells were all harvested at end point which is about two weeks post-RT. As shown in FIG. 8B, the IL-4/13 blocking peptide enhances the number of CD8+ T cells post radiation therapy.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A pharmaceutical composition comprising: a IL-4/IL-13 receptor inhibitor; and (ii) a pharmaceutically acceptable carrier, wherein the IL-4/IL-13 receptor inhibitor is CSRM53567 comprising of the amino acid sequence Tyr-Cys-Asp-Asp-Phe-Val-Gly-Ser-Phe-Asp-Cys-Tyr (SEQ ID NO: 1).

2. The composition of claim 1, wherein the IL-4/IL-13 receptor inhibitor is attached to moieties that result in PEGylation, glycosylation, lipidation, acetylation, amidation, end-capping modification, adding cyano groups, phosphorylation, or cyclization of the inhibitor.

3. The composition of claim 2, wherein the end-capping modification comprises acetylation at the N-terminus, N-terminal acylation, or N-terminal formylation.

4. The composition of claim 2, wherein the end-capping modification comprises amidation at the C-terminus, introduction of C-terminal alcohol, aldehyde, ester, or thioester moieties.

5. The composition of claim 1, wherein the IL-4/IL-13 receptor inhibitor is attached to moieties that result in extension of half-life of the inhibitor.

6. The composition of claim 5, wherein the moieties that result in extension of half-life of the inhibitor is Fc domain or serum albumin.

* * * * *

SEQUENCE LISTING

```
<160> NUMBER OF SEQ ID NOS: 59

<210> SEQ ID NO 1
<211> LENGTH: 12
<212> TYPE: PRT
<213> ORGANISM: Artificial Sequence
<220> FEATURE:
<223> OTHER INFORMATION: Peptide

<400> SEQUENCE: 1

Tyr Cys Asp Asp Phe Val Gly Ser Phe Asp Cys Tyr
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Peptide

<400> SEQUENCE: 2

Tyr Cys Asp Asp Phe Val Gly Ser Phe Asp Cys Tyr Asp
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Peptide

<400> SEQUENCE: 3

Tyr Cys Asp Asp Phe Val Gly Ser Phe Asp Cys Tyr Glu
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Peptide

<400> SEQUENCE: 4

Pro Lys Lys Lys Arg Lys Val
```

```
1               5

<210> SEQ ID NO 5
<211> LENGTH: 16
<212> TYPE: PRT
<213> ORGANISM: Artificial Sequence
<220> FEATURE:
<223> OTHER INFORMATION: Peptide

<400> SEQUENCE: 5

Lys Arg Pro Ala Ala Thr Lys Lys Ala Gly Gln Ala Lys Lys Lys Lys
1               5                   10                  15

<210> SEQ ID NO 6
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 6

Lys Lys Arg Xaa Lys Arg
1               5

<210> SEQ ID NO 7
<211> LENGTH: 18
<212> TYPE: PRT
<213> ORGANISM: Artificial Sequence
<220> FEATURE:
<223> OTHER INFORMATION: Peptide

<400> SEQUENCE: 7

Met Lys Trp Val Thr Phe Ile Ser Leu Leu Phe Leu Phe Ser Ser Ala
1               5                   10                  15

Tyr Ser

<210> SEQ ID NO 8
<211> LENGTH: 18
<212> TYPE: PRT
<213> ORGANISM: Artificial Sequence
<220> FEATURE:
<223> OTHER INFORMATION: Peptide

<400> SEQUENCE: 8

Met Ala Phe Leu Trp Leu Leu Ser Cys Trp Ala Leu Leu Gly Thr Thr
1               5                   10                  15

Gly Phe

<210> SEQ ID NO 9
<211> LENGTH: 14
<212> TYPE: PRT
<213> ORGANISM: Artificial Sequence
<220> FEATURE:
<223> OTHER INFORMATION: Peptide

<400> SEQUENCE: 9

Met Gln Leu Leu Ser Cys Ile Ala Leu Ile Leu Ala Leu Val
1               5                   10

<210> SEQ ID NO 10
<211> LENGTH: 15
<212> TYPE: PRT
```

<213> ORGANISM: Artificial Sequence
<220> FEATURE:
<223> OTHER INFORMATION: Peptide

<400> SEQUENCE: 10

Met Asn Leu Leu Leu Ile Leu Thr Phe Val Ala Ala Val Ala
1               5                  10                  15

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tggtgaagga aatgcgtaaa                                          20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gtcaatgatt cctgctcctg                                          20

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
agcagccttg gaatgtcttt ctcca                                    25

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
aggaacttcc tgccaatcca                                          20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
acaagcacac ccagtagcag                                          20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16

```
cctcctgccc tgctgggatg                                           20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
agaccacagt ctggcagttg                                           20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ccacccaaat gacacatagg                                           20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aagcatctct ggccacgcca                                           20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tgattacgag cagtggaagc                                           20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gttcaccgta agcccaattt                                           20

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
cacctggagt gatggttc                                             18

<210> SEQ ID NO 23
<211> LENGTH: 20
<212> TYPE: DNA
<213> ORGANISM: Artificial Sequence
```

<220> FEATURE:
<223> OTHER INFORMATION: Primer

<400> SEQUENCE: 23
actgagttcc tgcctctggt                                                    20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
atctgggacc aaggagagtg                                                    20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
cactgctgca cagggaagcc a                                                  21

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
cccagaaatc aaggagcatt                                                    20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tcactcttca cctgctccac                                                    20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tcgatgacag cgcctcagcc                                                    20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ccctatattt ggagcctgga                                                    20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
cttgcgaccc acgtagtaga                                          20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ccgcaggctt tggagccact                                          20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
accttgttca gctacgcctt                                          20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tcttcagagt ctgcccattg                                          20

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
tgctcctctt ccaaggtgct tgc                                      23

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ccaaagggat gagaagttcc                                          20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ctccacttgg tggtttgcta                                               20

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
tggcccagac cctcacactc a                                             21

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
ctccctggag aagagctacg                                               20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
tgactccatc ccaatgaaag                                               20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
aaacgaacgc ttccgctgcc                                               20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
agaaggccag tctggagaaa                                               20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
gagcccttga gacctctgac                                               20

<210> SEQ ID NO 43

```
<211> LENGTH: 20
<212> TYPE: DNA
<213> ORGANISM: Artificial Sequence
<220> FEATURE:
<223> OTHER INFORMATION: Primer

<400> SEQUENCE: 43
tgccctgggt cctcctggtc                                                   20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
tggtggccac taaatacgaa                                                   20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ggagggctaa cattctccag                                                   20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
caagcagacc agcccaggga                                                   20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
ccagaaatca acgagaccac                                                   20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ggcatatcca cagaggcttt                                                   20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
```

```
tctgcggcat ttcccacagc                                                   20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
tccttgcaat gtggatgttt                                                   20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
cttccagtac caaccgtcct                                                   20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tgcagagcgc cctggatctc                                                   20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
tgtgtccgtc gtggatctga                                                   20

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
cctgcttcac caccttcctt ga                                                22

<210> SEQ ID NO 55
<211> LENGTH: 26
<212> TYPE: DNA
<213> ORGANISM: Artificial Sequence
<220> FEATURE:
<223> OTHER INFORMATION: Primer

<400> SEQUENCE: 55
ccgcctggag aaacctgcca agtatg                                            26

<210> SEQ ID NO 56
<211> LENGTH: 4
<212> TYPE: PRT
```

```
<213> ORGANISM: Artificial Sequence
<220> FEATURE:
<223> OTHER INFORMATION: Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 56

Lys Lys Xaa Arg
1

<210> SEQ ID NO 57
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 57

Lys Lys Xaa Lys
1

<210> SEQ ID NO 58
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 58

Lys Arg Xaa Lys
1

<210> SEQ ID NO 59
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 59

Lys Arg Xaa Arg
1
```